US011591647B2

(12) United States Patent
Glezer et al.

(10) Patent No.: US 11,591,647 B2
(45) Date of Patent: Feb. 28, 2023

(54) NUCLEIC ACID SEQUENCING-BY-SYNTHESIS (SBS) METHODS THAT COMBINE SBS CYCLE STEPS

(71) Applicant: SINGULAR GENOMICS SYSTEMS, INC., La Jolla, CA (US)

(72) Inventors: Eli Glezer, Del Mar, CA (US); Andrew Spaventa, La Jolla, CA (US); David Barker, Del Mar, CA (US)

(73) Assignee: SINGULAR GENOMICS SYSTEMS, INC., San Diego, CA (US)

( * ) Notice: Subject to any disclaimer, the term of this patent is extended or adjusted under 35 U.S.C. 154(b) by 264 days.

(21) Appl. No.: 16/492,076

(22) PCT Filed: Mar. 6, 2018

(86) PCT No.: PCT/US2018/021219
§ 371 (c)(1),
(2) Date: Sep. 6, 2019

(87) PCT Pub. No.: WO2018/165207
PCT Pub. Date: Sep. 13, 2018

(65) Prior Publication Data
US 2020/0102609 A1 Apr. 2, 2020

Related U.S. Application Data

(60) Provisional application No. 62/467,751, filed on Mar. 6, 2017.

(51) Int. Cl.
*C12Q 1/6869* (2018.01)
*C07H 21/04* (2006.01)
*C12Q 1/6867* (2018.01)

(52) U.S. Cl.
CPC ........... *C12Q 1/6869* (2013.01); *C07H 21/04* (2013.01); *C12Q 1/6867* (2013.01); *C12Q 2521/101* (2013.01); *C12Q 2525/185* (2013.01); *C12Q 2525/186* (2013.01); *C12Q 2535/00* (2013.01)

(58) Field of Classification Search
CPC .................. C12Q 1/6869; C12Q 2525/186
See application file for complete search history.

(56) References Cited

U.S. PATENT DOCUMENTS

| 5,034,506 | A | 7/1991 | Summerton et al. |
|---|---|---|---|
| 5,235,033 | A | 8/1993 | Summerton et al. |
| 5,804,386 | A | 9/1998 | Ju |
| 5,814,454 | A | 9/1998 | Ju |
| 5,876,936 | A | 3/1999 | Ju |
| 5,952,180 | A | 9/1999 | Ju |
| 6,046,005 | A | 4/2000 | Ju et al. |
| 6,485,944 | B1 | 11/2002 | Church et al. |
| 6,627,748 | B1 | 9/2003 | Ju et al. |
| 6,664,079 | B2 | 12/2003 | Ju et al. |
| 7,074,597 | B2 | 7/2006 | Ju |
| 7,279,563 | B2 | 10/2007 | Kwiatkowski |
| 7,345,159 | B2 | 3/2008 | Ju et al. |
| 7,414,116 | B2 | 8/2008 | Milton et al. |
| 7,541,444 | B2 | 6/2009 | Milton et al. |
| 7,566,537 | B2 | 7/2009 | Barnes et al. |
| 7,622,279 | B2 | 11/2009 | Ju |
| 7,635,578 | B2 | 12/2009 | Ju et al. |
| 7,713,698 | B2 | 5/2010 | Ju et al. |
| 7,771,973 | B2 | 8/2010 | Milton et al. |
| 7,790,869 | B2 | 9/2010 | Ju et al. |
| 7,883,869 | B2 | 2/2011 | Ju et al. |
| 7,982,029 | B2 | 7/2011 | Ju et al. |
| 8,071,739 | B2 | 12/2011 | Milton et al. |
| 8,088,575 | B2 | 1/2012 | Ju et al. |
| 8,114,973 | B2 | 2/2012 | Siddiqi et al. |
| 8,298,792 | B2 | 10/2012 | Ju et al. |
| 8,399,188 | B2 | 3/2013 | Zhao et al. |
| 8,597,881 | B2 | 12/2013 | Milton et al. |
| 8,796,432 | B2 | 8/2014 | Ju et al. |
| 8,889,348 | B2 | 11/2014 | Ju |
| 8,900,810 | B2 | 12/2014 | Gordon et al. |
| 9,115,163 | B2 | 8/2015 | Ju et al. |
| 9,121,060 | B2 | 9/2015 | Milton et al. |
| 9,121,062 | B2 | 9/2015 | Balasubramanian et al. |
| 9,133,511 | B2 | 9/2015 | Ju et al. |
| 9,169,510 | B2 | 10/2015 | Ju et al. |
| 9,175,342 | B2 | 11/2015 | Ju et al. |
| 9,255,292 | B2 | 2/2016 | Ju et al. |
| 9,297,042 | B2 | 3/2016 | Ju et al. |
| 9,388,464 | B2 | 7/2016 | Milton et al. |

(Continued)

FOREIGN PATENT DOCUMENTS

| EP | 2876166 A1 | 5/2015 |
|---|---|---|
| EP | 2876166 B1 | 5/2015 |

(Continued)

OTHER PUBLICATIONS

Bentley, D.R. et al. (Nov. 6, 2008). "Accurate whole human genome sequencing using reversible terminator chemistry," *Nature* 456(7218):53-59.

Bergen, K. et al. (Jun. 17, 2013, e-published Jun. 3, 2013). "Structures of KOD and 9°N DNA polymerases complexed with primer template duplex," *Chembiochem* 14(9):1058-1062.

Bergseid, M. et al. (Nov. 2000). "Small molecule-based chemical affinity system for the purification of proteins," *BioTechniques* 29(5):1126-1133.

Binauld, S. et al. (Mar. 14, 2013). "Acid-degradable polymers for drug delivery: a decade of innovation," *Chem Commun* 49(21):2082-2102.

(Continued)

*Primary Examiner* — Samuel C Woolwine
(74) *Attorney, Agent, or Firm* — Mintz, Levin, Cohn, Ferris, Glovsky and Popeo, P.C.

(57) ABSTRACT

The present disclosure provides improved nucleic acid sequencing-by-synthesis (SBS) methods, related kits and reagents, and systems for performing such methods using such kits and reagents.

15 Claims, 1 Drawing Sheet

(56) References Cited

U.S. PATENT DOCUMENTS

| | | |
|---|---|---|
| 9,410,200 B2 | 8/2016 | Balasubramanian et al. |
| 9,528,151 B2 | 12/2016 | Ju et al. |
| 9,593,373 B2 | 3/2017 | Liu et al. |
| 9,624,539 B2 | 4/2017 | Ju et al. |
| 9,670,539 B2 | 6/2017 | Ju et al. |
| 9,708,358 B2 | 7/2017 | Ju et al. |
| 9,718,852 B2 | 8/2017 | Ju et al. |
| 9,719,139 B2 | 8/2017 | Ju et al. |
| 9,725,480 B2 | 8/2017 | Ju et al. |
| 9,868,985 B2 | 1/2018 | Ju et al. |
| 9,890,426 B2 | 2/2018 | Ju et al. |
| 10,000,801 B2 | 6/2018 | Ju et al. |
| 10,144,961 B2 | 12/2018 | Ju et al. |
| 10,190,157 B2 | 1/2019 | Wu et al. |
| 10,240,195 B2 | 3/2019 | Fuller et al. |
| 10,246,479 B2 | 4/2019 | Ju et al. |
| 10,260,094 B2 | 4/2019 | Ju et al. |
| 10,273,539 B2 | 4/2019 | Marma et al. |
| 10,336,785 B2 | 7/2019 | Marma et al. |
| 10,738,072 B1 | 8/2020 | Graham et al. |
| 10,822,653 B1 | 11/2020 | Graham et al. |
| 11,085,076 B2 | 8/2021 | Ju et al. |
| 2002/0015961 A1 | 2/2002 | Kwiatkowski |
| 2003/0027140 A1 | 2/2003 | Ju et al. |
| 2004/0023207 A1* | 2/2004 | Polansky ............. A61K 48/005 435/5 |
| 2006/0003383 A1 | 1/2006 | Graham |
| 2006/0057565 A1 | 3/2006 | Ju et al. |
| 2006/0188901 A1 | 8/2006 | Barnes et al. |
| 2006/0252038 A1 | 11/2006 | Ju |
| 2007/0009980 A1 | 1/2007 | Graham |
| 2007/0219367 A1 | 9/2007 | Shchepinov et al. |
| 2009/0047699 A1 | 2/2009 | Graham |
| 2011/0014611 A1 | 1/2011 | Ju et al. |
| 2012/0142006 A1 | 6/2012 | Ju et al. |
| 2012/0156671 A1 | 6/2012 | Liu et al. |
| 2012/0156680 A1 | 6/2012 | Ju et al. |
| 2013/0264207 A1 | 10/2013 | Ju et al. |
| 2013/0280700 A1 | 10/2013 | Ju et al. |
| 2015/0037788 A1 | 2/2015 | Ju |
| 2015/0080232 A1 | 3/2015 | Ju et al. |
| 2015/0140561 A1 | 5/2015 | Bergmann et al. |
| 2015/0197800 A1 | 7/2015 | Ju et al. |
| 2015/0368710 A1 | 12/2015 | Fuller et al. |
| 2016/0002721 A1 | 1/2016 | Liu et al. |
| 2016/0024570 A1 | 1/2016 | Ju et al. |
| 2016/0041179 A1 | 2/2016 | Ju et al. |
| 2016/0108382 A1 | 4/2016 | Efcavitch et al. |
| 2016/0208313 A1 | 7/2016 | Ju et al. |
| 2016/0264612 A1 | 9/2016 | Ju et al. |
| 2016/0265048 A1 | 9/2016 | Ju et al. |
| 2016/0355541 A1 | 12/2016 | Jain et al. |
| 2016/0369336 A1 | 12/2016 | Stupi et al. |
| 2017/0002407 A1 | 1/2017 | Balasubramanian et al. |
| 2017/0058335 A1 | 3/2017 | Tao et al. |
| 2017/0137869 A1 | 5/2017 | Marma et al. |
| 2017/0166961 A1 | 6/2017 | Liu et al. |
| 2017/0211134 A1 | 7/2017 | Marma et al. |
| 2017/0283451 A1 | 10/2017 | Ju et al. |
| 2018/0073071 A1 | 3/2018 | Ju et al. |
| 2018/0112257 A1 | 4/2018 | Ju et al. |
| 2018/0201642 A1 | 7/2018 | Ju et al. |
| 2018/0208774 A1 | 7/2018 | Marma et al. |
| 2018/0274024 A1 | 9/2018 | Ju et al. |
| 2018/0274025 A1 | 9/2018 | Marma et al. |
| 2018/0327828 A1 | 11/2018 | Ju et al. |
| 2019/0031704 A1 | 1/2019 | Ju et al. |
| 2019/0031705 A1 | 1/2019 | Ju et al. |
| 2019/0031706 A1 | 1/2019 | Ju et al. |
| 2019/0077726 A1 | 3/2019 | Graham et al. |
| 2019/0085014 A1 | 3/2019 | Ju et al. |
| 2019/0085015 A1 | 3/2019 | Ju et al. |
| 2019/0085016 A1 | 3/2019 | Ju et al. |
| 2019/0085388 A1 | 3/2019 | Ju et al. |
| 2019/0092805 A1 | 3/2019 | Ju et al. |
| 2019/0092806 A1 | 3/2019 | Ju et al. |
| 2019/0112650 A1 | 4/2019 | Ju et al. |
| 2019/0135850 A1 | 5/2019 | Ju et al. |
| 2019/0135851 A1 | 5/2019 | Ju et al. |
| 2019/0136308 A1 | 5/2019 | Ju et al. |
| 2019/0153527 A1 | 5/2019 | Ju et al. |

FOREIGN PATENT DOCUMENTS

| | | |
|---|---|---|
| EP | 3356381 A1 | 8/2018 |
| EP | 3356381 A4 | 8/2018 |
| WO | WO-02/022883 A1 | 3/2002 |
| WO | WO-02/029003 A2 | 4/2002 |
| WO | WO-02/029003 A3 | 4/2002 |
| WO | WO-2008/037568 A2 | 4/2008 |
| WO | WO-2008/037568 A3 | 4/2008 |
| WO | WO-2018/165207 A1 | 9/2008 |
| WO | WO-2009/054922 A1 | 4/2009 |
| WO | WO-2012/083249 A2 | 6/2012 |
| WO | WO-2012/083249 A3 | 6/2012 |
| WO | WO-2012/162429 A2 | 11/2012 |
| WO | WO-2012/162429 A3 | 11/2012 |
| WO | WO-2013/154999 A2 | 10/2013 |
| WO | WO-2013/154999 A3 | 10/2013 |
| WO | WO-2013/191793 A1 | 12/2013 |
| WO | WO-2014/144883 A1 | 9/2014 |
| WO | WO-2014/144898 A1 | 9/2014 |
| WO | WO-2015/123430 A2 | 8/2015 |
| WO | WO-2015/123430 A3 | 8/2015 |
| WO | WO-2015/148402 A1 | 10/2015 |
| WO | WO-2016/063059 A1 | 4/2016 |
| WO | WO-2016/144973 A1 | 9/2016 |
| WO | WO-2016/154215 A1 | 9/2016 |
| WO | WO-2017/058953 A1 | 4/2017 |
| WO | WO-2017/079498 A2 | 5/2017 |
| WO | WO-2017/079498 A3 | 5/2017 |
| WO | WO-2017/087887 A1 | 5/2017 |
| WO | WO-2017/176677 A1 | 10/2017 |
| WO | WO-2017/176679 A1 | 10/2017 |
| WO | WO-2017/205336 A1 | 11/2017 |
| WO | WO-2018/183538 A1 | 10/2018 |
| WO | WO-2019/105421 A1 | 6/2019 |
| WO | WO-2019/164977 A1 | 8/2019 |
| WO | WO-2020/086834 A1 | 4/2020 |
| WO | WO-2020/146397 A1 | 7/2020 |
| WO | WO-2020/146497 A1 | 7/2020 |

OTHER PUBLICATIONS

Blackman, M.L. et al. (Oct. 15, 2008, e-published Sep. 18, 2008). "The Tetrazine ligation: fast bioconjugation based on inverse-electron-demand Diels-Alder reactivity," *J Am Chem Soc* 130(41):13518-13519.

Debets, M.F. et al. (Oct. 14, 2013, e-published Aug. 23, 2013). "Bioorthogonal labelling of biomolecules: new functional handles and ligation methods," *Org Biomol Chem* 11(38):6439-6455.

Extended European Search Report dated May 10, 2019, for EP Patent Application No. 16852516.0, 7 pages.

Fuller, C.W. et al. (May 10, 2016, e-published Apr. 18, 2016). "Real-time single-molecule electronic DNA sequencing by synthesis using polymer-tagged nucleotides on a nanopore array," *PNAS USA* 113(19):5233-5238.

Guo, J. et al. (Jul. 8, 2008, e-published Jun. 30, 2008). "Four-color DNA sequencing with 3'-O-modified nucleotide reversible terminators and chemically cleavable fluorescent dideoxynucleotides," *PNAS USA* 105(27):9145-9150.

Hutter, D. et al. (Nov. 2010). "Labeled nucleoside triphosphates with reversibly terminating aminoalkoxyl groups," *Nucleosides Nucleotides Nucleic Acids* 29(11):879-895.

Inoue, T. et al. (Nov. 2015). "Synthesis of trifluoromethyl ethers and difluoro(methylthio)methyl ethers by the reaction of dithiocarbonates with $IF_5$-pyridine-HF," *Journal of Fluorine Chemistry* 179:48-52.

International Search Report dated Dec. 29, 2016, for PCT Application No. PCT/US2016/054236, filed Sep. 28, 2016, 4 pages.

(56) References Cited

OTHER PUBLICATIONS

International Search Report dated Jun. 1, 2018 for PCT Application No. PCT/US2018/021219, filed Mar. 6, 2018, 3 pages.
International Search Report dated Jun. 25, 2019, for PCT Application No. PCT/US2019/018810, filed Feb. 20, 2019, 4 pages.
International Search Report dated Jan. 6, 2020 for PCT Application No. PCT/US2019/57842, filed Oct. 24, 2019, 3 pages.
Jewett, J.C. et al. (Mar. 24, 2010). "Rapid Cu-free click chemistry with readily synthesized biarylazacyclooctynones," *J Am Chem Soc* 132(11):3688-3690.
Ju, J. et al. (Dec. 26, 2006, e-published Dec. 14, 2006). "Four-color DNA sequencing by synthesis using cleavable fluorescent nucleotide reversible terminators," *PNAS USA* 103(52):19635-19640.
Kumar, S. et al. (2012, e-published Sep. 21, 2012). "PEG-labeled nucleotides and nanopore detection for single molecule DNA sequencing by synthesis," *Sci Rep* 2:684.
Leriche, G. et al. (Jul. 2010). "Optimization of the Azobenzene Scaffold for Reductive Cleavage by Dithionite; Development of an Azobenzene Cleavable Linker for Proteomic Applications," *Eur J Org Chem* 2010(23):4360-4364.
Marcus-Sekura, C.J. et al. (Aug. 1, 1988). "Techniques for using antisense oligodeoxyribonucleotides to study gene expression," *Anal Biochem* 172(2):289-295.
Needleman, S.B .et al. (Mar. 1970). "A general method applicable to the search for similarities in the amino acid sequence of two proteins," *J Mol Biol* 48(3):443-453.
Pearson, W.R. et al. (Apr. 1988). "Improved tools for biological sequence comparison," *PNAS USA* 85(8):2444-2448.
PubChem Compound Summary for CID 121486816 (Aug. 16, 2016). Located at <https:pubchem.ncbi.nlm.nih.gov/compound/121486816> last visited Apr. 22, 2019, 7 pages.
PubChem Compound Summary for CID 69188114 (Nov. 30, 2012). Located at <https:pubchem.ncbi.nlm.nih.gov/compound/69188114> last visited Apr. 22, 2019, 7 pages.
Rathod, K.M. et al. (2013). "Synthesis and Antimicrobial Activity of Azo Compounds Containing m-Cresol Moiety," *Chem Sci Trans* 2(1):25-28.
Rosenblum, B.B. et al. (Nov. 15, 1997). "New dye-labeled terminators for improved DNA sequencing patterns," *Nucleic Acids Res* 25(22):4500-4504.
Ruparel, H. et al. (Apr. 26, 2005, e-published Apr. 13, 2005). "Design and synthesis of a 3'-O-allyl photocleavable fluorescent nucleotide as a reversible terminator for DNA sequencing by synthesis," *PNAS USA* 102(17):5932-5937.
Schumacher, W. et al. (Jun. 16, 1997). "Redox chemistry of cobalamin and iron-sulfur cofactors in the tetrachloroethene reductase of *Dehalobacter restrictus*," *FEBS Lett* 409(3):421-425.
Shenoi, R.A. et al. (Sep. 12, 2012, e-published Aug. 30, 2012). "Branched multifunctional polyether polyketals: variation of ketal group structure enables unprecedented control over polymer degradation in solution and within cells," *J Am Chem Soc* 134(36):14945-14957.
Smith T.F. et al. (Dec. 1981). "Comparison of biosequences," *Advances in Applied Mathematics* 2(4):482-489.
Southworth, M.W. et al. (May 28, 1996). "Cloning of thermostable DNA polymerases from hyperthermophilic marine Archaea with emphasis on *Thermococcus* sp. 9°N-7 and mutations affecting 3'-5' exonuclease activity," *PNAS USA* 93(11):5281-5285.
Švagera, Z. et al. (Mar. 2012, e-published Feb. 15, 2012). "Study of disulfide reduction and alkyl chloroformate derivatization of plasma sulfur amino acids using gas chromatography-mass spectrometry," *Anal Bioanal Chem* 402(9):2953-2963.
Uhlmann, E. et al. (Jun. 1990). "Antisense oligonucleotides: a new therapeutic principle," *Chemical Reviews* 90(4):543-584.
Weintraub, H.M. (Jan. 1990). "Antisense RNA and DNA," *Sci Am* 262(1):40-46.
Written Opinion dated Dec. 29, 2016, for PCT Application No. PCT/US2016/054236, filed Sep. 28, 2016, 4 pages.
Written Opinion dated Jun. 1, 2018 for PCT Application No. PCT/US2018/021219, filed Mar. 6, 2018, 9 pages.
Written Opinion dated Jun. 25, 2019, for PCT Application No. PCT/US2019/018810, filed Feb. 20, 2019, 5 pages.
Written Opinion dated Jan. 6, 2020 for PCT Application No. PCT/US2019/57842, filed Oct. 24, 2019, 11 pages.
Wu, J. et al. (Oct. 16, 2007, e-published Oct. 8, 2007). "3'-O-modified nucleotides as reversible terminators for pyrosequencing," *PNAS USA* 104(42):16462-16467.
Zhu, Z. et al. (Aug. 25, 1994). "Directly labeled DNA probes using fluorescent nucleotides with different length linkers," *Nucleic Acids Res* 22(16):3418-3422.
Guillier, F. et al. (Jun. 14, 2000). "Linkers and cleavage strategies in solid-phase organic synthesis and combinatorial chemistry," *Chem Rev* 100(6):2091-2158.
International Search Report dated Apr. 2, 2020 for PCT Application No. PCT/US2020/012595, filed Jan. 7, 2020, 3 pages.
Written Opinion dated Apr. 2, 2020 for PCT Application No. PCT/US2020/012595, filed Jan. 7, 2020, 3 pages.

* cited by examiner

NUCLEIC ACID SEQUENCING-BY-SYNTHESIS (SBS) METHODS THAT COMBINE SBS CYCLE STEPS

CROSS REFERENCE TO RELATED APPLICATIONS

The present application is the national state filing under U.S.C. 371 of International Application No. PCT/US18/21219, filed Mar. 6, 2018, which claims priority to U.S. Provisional Application No. 62/467,751, filed Mar. 6, 2017, the disclosure of which are hereby incorporated by reference in their entirety.

FIELD OF THE INVENTION

The present disclosure generally relates to nucleic acid sequencing, particularly to improved devices, systems, and methods for nucleic acid sequencing with combined cycle steps, for example to shorten cycle times.

BACKGROUND OF THE INVENTION

DNA sequencing is a key technology in genomics research, and is becoming more important in drug discovery and medicine. Accurate, high-throughput, low cost DNA sequencing methods are thus required. The Human Genome Project, which resulted in sequencing the first human genome in 2001, took 15 years and $3 billion to complete using electrophoresis-based sequencing technology.

Since then, a number of new automated DNA-sequencing technologies have been developed, including sequence-specific detection of single-stranded DNA using engineered nanopores and sequencing by ligation. More recently, DNA sequencing-by-synthesis (SBS) approaches have become prevalent, and are used for sequencing whole large (e.g., human, plant) and small (e.g., bacterial, viral) genomes, exomes, whole or partial transcriptomes, and targeted genes, as well as gene expression profiling, micro and small RNA analysis, DNA-protein interaction analysis, epigenetic (e.g., methylation) analysis, etc.

Today, SBS schemes based on fluorescence detection in a chip format represent the state of the art. In a typical SBS process, many millions to billions of DNA fragments are sequenced in a massively parallel fashion. For a given genome, this is accomplished by preparing a sequencing library through random fragmentation of a DNA or cDNA sample followed by 5' and 3' adapter ligation. PCR is then used to amplify the number of DNA molecules in the library, followed by purification. The library is then denatured and loaded into a flow cell where fragments are captured on a lawn of surface-bound oligonucleotides complementary to the library adapters. Each captured fragment is then amplified through isothermal bridge amplification into a distinct, clonal cluster containing 100's to 1000's of template DNA molecules of identical nucleotide sequence, with the flow cell containing millions to billions of such clusters. When cluster generation in the flow cell is complete, the templates in the clusters are ready for sequencing, and today, up to six trillion bases (terabases) can be sequenced in a single run. At each step of nucleotide base addition in an SBS cycle, DNA polymerase catalyzes the incorporation of fluorescently labeled, reversibly blocked deoxyribonucleotide triphosphate (dNTP) terminators into growing DNA strands. After the base incorporation step, the flow cell is imaged and the emission spectra from each cluster is recorded. The emission wavelength and intensity for each cluster are used to identify the particular base added in a given cycle. After imaging, the labels and reversible terminating moieties on the newly incorporated dNTPs are then cleaved, regenerating strands (i.e., extension products) that can then be extended in a subsequent SBS cycle. This cycle is repeated "n" times to create a read length of "n" bases for all of the clusters in the flow cell. After the desired number of SBS cycles is performed, the nucleotide sequences for the clusters (the nucleotide sequence of each cluster being a "read") are aligned to a reference sequence and assembled into a larger sequence using bioinformatics software. If desired, differences (if any) between the reference genome and the newly sequenced DNA sample can then be identified using bioinformatics software.

As the foregoing makes clear, conventional SBS approaches involve performing a number of steps in series for each SBS cycle. Today, each SBS cycle takes on the order of 5-30 minutes to perform, and run times of 4-30 hours are typical for analysis of reads containing 150 nucleotides. While this timing represents a tremendous advance, the need still exists for even shorter cycle and total run times. The present disclosure addresses this and other needs.

SUMMARY OF THE INVENTION

The present disclosure concerns improved nucleic acid sequence-by-synthesis (SBS) methods that shorten SBS cycle times. Thus, in one aspect, the present disclosure provides methods to determine the identity of a nucleotide residue in an extension product. Such methods include (a) combining in a sequencing reaction mixture a plurality of identical primed template DNA molecules, a DNA polymerase, at least 4 distinguishable, blocked deoxyribonucleotide triphosphate (dNTP) analogue species, at least 3 of which are labeled such that various distinguishable, blocked dNTP analogue species can be distinguished from the other such species, under conditions to allow incorporation of one of the distinguishable, blocked dNTP analogue species into at least one of the plurality of identical primed template DNA molecules to form a (or a population of) distinguishable, blocked extension product(s); (b) after step (a), adding to the sequencing reaction mixture at least 4 unlabeled, blocked dNTP analogue species under chasing conditions (i.e., conditions under which an unlabeled, blocked dNTP analogue species can be incorporated into a primed template DNA molecule that was not extended in step (a) to include a distinguishable, blocked dNTP analogue species), thereby forming a (or a population of) unlabeled, blocked extension product(s); and (c) during step (a) and/or (b), determining the identity of the distinguishable, blocked dNTP analogue incorporated into the labeled, blocked extension product(s) in step (a).

In embodiments, such methods include (a) combining in a sequencing reaction mixture a plurality of identical primed template DNA molecules, a DNA polymerase, four (or five) species of labeled, 3'-blocked dNTP analogues, such as a labeled, 3'-blocked dGTP analogue, a labeled, 3'-blocked dATP analogue, a labeled, 3'-blocked dCTP analogue, and a labeled, 3'-blocked dTTP analogue and/or a labeled, 3'-blocked dUTP analogue under conditions to allow incorporation of one of the labeled, 3'-blocked dNTP species into at least one of the plurality of identical primed template DNA molecules to form a (or a population of) labeled, blocked extension product(s); (b) after step (a), adding to the sequencing reaction mixture four (or five) species of unlabeled, 3'-blocked dNTPs, such as an unlabeled, 3'-blocked dGTP analogue, an unlabeled, 3'-blocked dATP analogue, an unlabeled, 3'-blocked dCTP analogue, and an unlabeled, 3'-blocked dTTP analogue and/or an unlabeled, 3'-blocked dUTP analogue, under chasing conditions, i.e., to allow incorporation of one of the unlabeled, 3'-blocked dNTP species into one or more of the plurality of identical primed template DNA molecules into which a labeled, 3'-blocked dNTP analogue was not incorporated, to form a (or a population of) unlabeled 3'-blocked extension product(s); and (c) during step (a) and/or (b), determining the identity of the labeled, 3'-blocked dNTP analogue incorporated into the labeled, blocked extension product(s) in step (a).

In embodiments, the method further comprises assigning the complement of the labeled, 3'-blocked dNTP analogue determined in step (c) as the identity of the nucleotide residue in the template DNA molecule. In other embodiments, the identity of the labeled, 3'-blocked dNTP analogue is assigned as the identity of the nucleotide residue. This process may be iterated one or more times.

In embodiments, the methods of the present disclosure further comprise treating the labeled and unlabeled, blocked extension products to generate extendible (i.e., not blocked) extension products. That is, the labeled and unlabeled, blocked extension products are treated to remove the 3' blocking group such that the extension products are extendible. Representative examples of such treatment include cleavage, optionally chemical, enzymatic, or photoactivated cleavage, of a blocking moiety linked to a 3'-oxygen atom of a terminal deoxyribose of the labeled, blocked extension products and unlabeled, blocked extension products (if any).

In embodiments, the methods further comprise removing unbound labeled, 3'-blocked dNTP analogues after step (a) but before step (b).

Embodiments of this aspect involve iterating steps (a)-(c) one or more times, wherein after step (c) of each iteration, the labeled, blocked extension products and unlabeled, blocked extension products are treated to generate extendible extension products, with the proviso that after the last iteration, treatment of the labeled and unlabeled, blocked extension products can be omitted.

In embodiments, the labeled, 3'-blocked dNTP analogues are a labeled, 3'-blocked dGTP analogue, a labeled, 3'-blocked dCTP analogue, a labeled, 3'-blocked dATP analogue, and a labeled, 3'-blocked dTTP analogue and/or a labeled, 3'-blocked dUTP analogue, wherein optionally the labeled, 3'-blocked dGTP, dCTP, dATP, dTTP, and/or dUTP analogue(s) comprise an incorporable nucleoside or incorporable analogue thereof, wherein optionally such incorporable nucleoside or incorporable analogue thereof comprises a base selected from the group consisting of guanine (in the case of a labeled, 3'-blocked dGTP analogue), cytosine (in the case of a labeled, 3'-blocked dCTP analogue), adenine (in the case of a labeled, 3'-blocked dATP analogue), thymine (in the case of a labeled, 3'-blocked dTTP analogue), or uracil (in the case of a labeled, 3'-blocked dUTP analogue); the labeled, 3'-blocked dGTP, dCTP, dATP, dTTP, and/or dUTP analogue(s) comprise a sugar moiety that is deoxyribose or a deoxyribose analogue; the labeled, 3'-blocked dGTP, dCTP, dATP, dTTP, and/or dUTP analogue(s) comprise a cleavable blocking moiety, wherein the cleavable blocking moiety optionally is linked to the 3'-position of the sugar moiety, wherein the sugar moiety optionally is deoxyribose or a deoxyribose analogue, and/or each of the labeled, 3'-blocked dNTP analogue species is distinguishable from the other labeled, 3'-blocked dNTP analogue species by inclusion of a unique label molecule that differs from the unique label molecules of the other labeled, 3'-blocked dNTP analogue species, wherein the label molecules are optionally selected from the group consisting of a dye, a chromophore, a combinatorial fluorescence energy transfer label, an electrophore, a fluorophore, a mass label, and a radiolabel, wherein optionally the cleavable blocking moiety is linked to the 3'-position of the sugar moiety (optionally a deoxyribose or a deoxyribose analogue) and comprises the unique label molecule.

Labeled, 3'-blocked dNTP analogues that may be used in the methods described herein include, without limitation, 3'-O-allyl-dGTP-allyl-Cy5, 3'-O-allyl-dCTP-allyl-Bodipy-FL-510, 3'-O-allyl-dATP-allyl-ROX, and 3'-O-allyl-dUTP-allyl-R6G; 3'-O-allyl-dGTP-allyl-Bodipy-FL-510, 3'-O-allyl-dCTP-allyl-Bodipy-650, 3'-O-allyl-dATP-allyl-ROX, and 3'-O-allyl-dUTP-allyl-R6G; and 3'-O-allyl-dGTP-allyl-Bodipy-650, 3'-O-allyl-dCTP-allyl-Bodipy-FL-510, 3'-O-allyl-dATP-allyl-ROX, and 3'-O-allyl-dUTP-allyl-R6G. Labels may include, but are not limited to, fluorescein-based dyes, Alexa dyes, Atto dyes, Rhodamine-based dyes, Cyanine-based dyes, and Si-Rhodamine-based dyes.

In embodiments, the unlabeled, 3'-blocked dNTP analogue species are an unlabeled, 3'-blocked dGTP, an unlabeled, 3'-blocked dCTP, an unlabeled, 3'-blocked dATP, and an unlabeled, 3'-blocked dTTP or an unlabeled, 3'-blocked dUTP, wherein optionally the unlabeled, 3'-blocked dNTPs comprise an incorporable nucleoside or incorporable analogue thereof, wherein optionally such incorporable nucleoside or incorporable analogue thereof comprises guanine (in the case of an unlabeled, 3'-blocked dGTP), cytosine (in the case of an unlabeled, 3'-blocked dCTP), adenine (in the case of an unlabeled, 3'-blocked dATP), thymine (in the case of an unlabeled, 3'-blocked dTTP), or uracil (in the case of an unlabeled, 3'-blocked dUTP), the unlabeled, 3'-blocked dNTP analogues comprise a sugar moiety that is deoxyribose or a deoxyribose analogue, and/or the unlabeled, 3'-blocked dNTP analogues comprise a cleavable blocking moiety, wherein the cleavable blocking moiety optionally is linked to the 3'-position of the sugar moiety, wherein the sugar moiety optionally is deoxyribose or a deoxyribose analogue. In embodiments, the cleavable blocking moiety of the unlabeled, 3'-blocked dNTP analogues is linked to the 3'-oxygen of a deoxyribose via an allyl moiety or a 2-nitrobenzyl moiety.

Unlabeled, 3'-blocked dNTP analogues that may be used in the methods described herein include 3'-O-allyl-dGTP, 3'-O-allyl-dCTP, 3'-O-allyl-dATP, and 3'-O-allyl-dUTP; and 3'-O-2-nitrobenzyl-dGTP, 3'-O-2-nitrobenzyl-dCTP, 3'-O-2-nitrobenzyl-dATP, and 3'-O-2-nitrobenzyl-dUTP.

In embodiments, step (b) is initiated before step (a) is completed.

In embodiments, the template DNA molecules are either in solution or immobilized on a solid substrate, wherein the solid substrate optionally is glass or plastic and optionally is configured as a bead, chip, or slide, and wherein the DNA template molecules optionally are (i) bound to the solid substrate via polyethylene glycol (PEG) molecules and the solid substrate is azide-functionalized or (2) immobilized on the solid substrate via an azido linkage, an alkynyl linkage, or a biotin-streptavidin interaction.

In embodiments of the methods of the present disclosure, the DNA polymerase is a 9° N polymerase or variant thereof. See, e.g., U.S. Pat. No. 5,756,334, which is incorporated herein by reference in its entirety.

In embodiments of the methods of the present disclosure, the cleavable blocking moiety of the labeled, 3'-blocked dNTP analogues is linked to the 3'-oxygen of a deoxyribose via an allyl moiety or a 2-nitrobenzyl moiety.

In a related aspect, the present disclosure provides nucleic acid sequencing-by-synthesis methods for a DNA template molecule, comprising iterating steps (a)-(c), above, two or more times; after each iteration, treating the labeled, 3'-blocked extension products and unlabeled, 3'-blocked extension products to generate extendible, unlabeled extension products, with the proviso that after the last iteration, treatment of the labeled, 3'-blocked extension products and unlabeled, 3'-blocked extension products can be omitted; for each iteration, assigning the complement of the labeled, 3'-blocked dNTP analogue determined in step (c) as the identity of the nucleotide residue in the template DNA molecule for that iteration; and assembling in order (optionally 5' to 3') the identities of the nucleotide residues of the template DNA molecule, thereby determining by synthesis the nucleotide sequence of the template DNA molecule.

In another aspect, the present disclosure provides kits for performing a method according to the present disclosure. In general, such kits will include, optionally in separate containers or compartments, (a) labeled, 3'-blocked dNTP analogues, for example, labeled, 3'-blocked dGTP, dATP, dCTP, and dTTP and/or dUTP analogues, (b) unlabeled, 3'-blocked dNTP analogues, for example, unlabeled, 3'-blocked dGTP, dATP, dCTP, and dTTP and/or dUTP analogues, (c) reagents suitable for use in DNA synthesis, and (d) instructions (or a link other reference to a website providing such instructions) for using such dNTP analogues and reagents to perform a method of the present disclosure.

The foregoing and other objects, features, and advantages of the present disclosure will be apparent from the following detailed description and the claims.

BRIEF DESCRIPTION OF THE DRAWINGS

FIG. 1 represents the first 10 cycles of four color SBS data for a fragment of the PhiX 174 DNA immobilized on beads in a flow cell. The graph shows fluorescence emission intensity obtained by using a mixture of 4 labeled, blocked dNTPs: dCTP-Bodipy, dTTP-R6G, dATP-AF568, dGTP-AF647. The fluorescence images were taken during the chase step, as dark, blocked dNTPs were being incorporated into any remaining previously unextended complementary DNA strands.

DETAILED DESCRIPTION OF THE INVENTION

Currently available "next generation sequencing" (NGS) technology has permitted the rapid and relatively economical acquisition of data that has driven the widespread adoption of this valuable research and diagnostic tool. Indeed, since the announcement in 2000 of the first sequencing of the human genome, the cost of sequencing a human genome has dropped to about $1,000. In the same time interval, the required time to sequence a human genome has decreased from 10 years to about 26 hours. Despite these substantial improvements, there remains significant unmet need to improve the speed and accuracy of DNA sequencing to increase the availability of high quality data and to permit a wider adoption of sequencing as a diagnostic technology. Current technologies that permit high-throughput sequencing include "2nd generation" sequencing by synthesis (SBS) technologies from Illumina and Thermo-Fisher. These technologies have many drawbacks, including long cycle times (5-30 minutes), which prevent the generation of rapid sequencing results.

I. Definitions

Before describing the instant disclosure in detail, several terms used in the context of the present disclosure will be defined. In addition to these terms, others are defined elsewhere in the specification, as necessary. Unless otherwise expressly defined herein, terms of art used in this specification will have their art-recognized meanings.

The term "analogue", in reference to a chemical compound, refers to compound having a structure similar to that of another one, but differing from it in respect of one or more different atoms, functional groups, or substructures that are replaced with one or more other atoms, functional groups, or substructures. In the context of a nucleotide useful in practicing the present disclosure, a nucleotide analog refers to a compound that, like the nucleotide of which it is an analog, can be incorporated into a nucleic acid molecule (e.g., an extension product) by a suitable polymerase, for example, a DNA polymerase in the context of a dNTP analogue.

The term "blocking moiety" or "blocking group" refers to a chemical group that, when attached to a nucleotide, inhibits further extension of a nucleic acid (e.g., inhibits addition of one or more nucleotides to the nucleic acid) when the nucleotide is incorporated into the nucleic acid. Such structural modification ("blocking group") of the sequencing nucleotides ensures a single nucleotide incorporation but then prevents any further nucleotide incorporation into the polynucleotide chain. The blocking group is then removable, under reaction conditions which do not interfere with the integrity of the DNA being sequenced. Where extension of a nucleic acid is inhibited due to a blocking group attached to a nucleotide within the nucleic acid, the nucleotide may be referred to as "blocked." The chemical group can inhibit extension by a catalyst such as a polymerase, ligase, terminal transferase, reverse transcriptase, polynucleotide phosphorylase, telomerase, or the like. Typically, the blocking group prevents attachment of the 3' hydroxyl to the 5' phosphate of another nucleotide. The blocking group in a nucleotide may sometimes be referred to as a "terminator" since the extension reaction by the catalyst is inhibited, also referred to herein as "terminated." A terminator can also be referred to as a "non-extendible" nucleotide analogue since, upon incorporation into a nucleic acid, it prevents further extension of the nucleic acid, for example, by a DNA polymerase that, in the absence of the blocking moiety, could catalyze incorporation of the dNTP analogue into the nucleic acid.

The term "chromophore" refers to an atom or group whose presence is responsible for the color of a compound.

The term "combinatorial fluorescence energy transfer label" refers to labels that exploit optical interactions that persist between two chromophores even when they are as far as 80 angstroms apart. The chromophore with high energy absorption is defined as a donor, and the chromophore with lower energy absorption is defined as an acceptor. Fluorescence energy transfer is mediated by a dipole-dipole coupling between the chromophores that results in resonance transfer of excitation energy from an excited donor molecule to an acceptor. See, e.g., published U.S. patent application publication no. 20060057565, which is incorporated herein by reference in its entirety.

The term "complexity", in reference to a population of molecules, e.g., polynucleotides, means that a number of different species of the molecule (e.g., polynucleotides having different nucleotide sequences, sizes, etc.) are present in the population.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanidine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

The term "dye" refers to a chemical label that can be added to another substance to add a color that can be detected. Examples of dyes include fluorescent dyes, including FAM, Bodipy, TAMRA, and Alexa dyes.

"DNA" refers to deoxyribonucleic acid, a polymer of deoxyribonucleotides (e.g., adenine, guanine, cytosine, thymine, uricil, etc.) linked by phosphodiester bonds. DNA can be single-stranded (ssDNA) or double-stranded (dsDNA), and can include both single and double-stranded (or "duplex") regions. "RNA" refers to ribonucleic acid, a polymer of ribonucleotides linked by phosphodiester bonds. RNA can be single-stranded (ssRNA) or double-stranded (dsRNA), and can include both single and double-stranded (or "duplex") regions. Single-stranded DNA (or regions thereof) and ssRNA can, if sufficiently complementary, hybridize to form double-stranded complexes (or regions).

The term "DNA template" refers to any DNA molecule that may be bound by a DNA polymerase and utilized as a template for nucleic acid synthesis.

The term "dATP analogue" refers to an analogue of deoxyadenosine triphosphate (dATP) that is a substrate for a DNA polymerase.

The term "dCTP analogue" refers to an analogue of deoxycytidine triphosphate (dCTP) that is a substrate for a DNA polymerase.

The term "dGTP analogue" refers to an analogue of deoxyguanosine triphosphate (dGTP) that is a substrate for a DNA polymerase.

The term "dNTP analogue" refers to an analogue of deoxynucleoside triphosphate (dNTP) that is a substrate for a DNA polymerase The term "dTTP analogue" refers to an analogue of deoxythymidine triphosphate (dUTP) that is a substrate for a DNA polymerase.

The term "dUTP analogue" refers to an analogue of deoxyuridine triphosphate (dUTP) that is a substrate for a DNA polymerase.

The term "extendible" means, in the context of a nucleotide, primer, or extension product, that the 3'-OH group of the particular molecule is available and accessible to a DNA polymerase for addition of a dNTP or dNTP analogue.

The term "fluorophore" means a fluorescent chemical compound that can re-emit light upon light excitation. Fluorophores include, for example, fluorescent lanthanide complexes, including those of Europium and Terbium, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue™, Texas Red, Alexa dyes, phycoerythin, Bodipy, and others known in the art, see, e.g., Haugland, Molecular Probes Handbook (Eugene, Oreg.), 6th Edition; The Synthegen catalog (Houston, Tex.); Lakowicz, Principles of Fluorescence Spectroscopy, 2nd Ed., Plenum Press New York (1999), and WO 98/59066, each of which is incorporated herein by reference in its entirety.

The term "identical", in the context of, for example, a particular set of "template DNA molecules" (e.g., the DNA molecules in a particular "cluster" on an NGS flow cell), will mean that all such molecules have the same nucleotide sequence.

The terms "iterating" and the like mean to repeat.

The term "label" refers to one or more atoms (e.g. a detectable moiety) that can be specifically detected to indicate the presence of a substance to which the one or more atoms is attached. The label may be detectable by spectroscopic, photochemical, biochemical, immunochemical, chemical, magnetic resonance imaging, or other physical means. A label can be a primary label that is directly detectable or secondary label that can be indirectly detected, for example, via direct or indirect interaction with a primary. Labels includes dyes, chromophores, combinatorial fluorescence energy transfer labels, electrophores, fluorophores, mass labels, and radiolabels. For example, detectable labels include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99}$mTc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), modified oligonucleotides (e.g., moieties described in PCT/US2015/022063, which is incorporated herein by reference), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorocarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide.

Examples of detectable agents include imaging agents, including fluorescent and luminescent substances, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescein isothiocyanate moiety, tetramethylrhodamine-5-(and 6)-isothiocyanate moiety, Cy2 moeity, Cy3 moiety, Cy5 moiety, Cy7 moiety, 4',6-diamidino-2-phenylindole moiety, Hoechst 33258 moiety, Hoechst 33342 moiety, Hoechst 34580 moiety, propidium-iodide moiety, or acridine orange moiety. In embodiments, the detectable moiety is a Indo-1, Ca saturated moiety, Indo-1 Ca2+ moiety, Cascade Blue BSA pH 7.0 moiety, Cascade Blue moiety, LysoTracker Blue moiety, Alexa 405 moiety, LysoSensor Blue pH 5.0 moiety, LysoSensor Blue moiety, DyLight 405 moiety, DyLight 350 moiety, BFP (Blue Fluorescent Protein) moiety, Alexa 350 moiety, 7-Amino-4-methylcoumarin pH 7.0 moiety, Amino Coumarin moiety, AMCA conjugate moiety, Coumarin moiety, 7-Hydroxy-4-methylcoumarin moiety, 7-Hydroxy-4-methylcoumarin pH 9.0 moiety, 6,8-Difluoro-7-hydroxy-4-methylcoumarin pH 9.0 moiety, Hoechst 33342 moiety, Pacific Blue moiety, Hoechst 33258 moiety, Hoechst 33258-DNA moiety, Pacific Blue antibody conjugate pH 8.0 moiety, PO-PRO-1 moiety, PO-PRO-1-DNA moiety, POPO-1 moiety, POPO-1-DNA moiety, DAPI-DNA moiety, DAPI moiety, Marina Blue moiety, SYTOX Blue-DNA moiety, CFP (Cyan Fluorescent Protein) moiety, eCFP (Enhanced Cyan Fluorescent Protein) moiety, 1-Anilinonaphthalene-8-sulfonic acid (1,8-ANS) moiety, Indo-1, Ca free moiety, 1,8-ANS (1-Anilinonaphthalene-8-sulfonic acid) moiety, BO-PRO-1-DNA moiety, BOPRO-1 moiety, BOBO-1-DNA moiety, SYTO 45-DNA moiety, evoglow-Pp1 moiety, evoglow-Bs1 moiety, evoglow-Bs2 moiety, Auramine O moiety, DiO moiety, LysoSensor Green pH 5.0 moiety, Cy 2 moiety, LysoSensor Green moiety, Fura-2, high Ca moiety, Fura-2 Ca2+sup> moiety, SYTO 13-DNA moiety, YO-PRO-1-DNA moiety, YOYO-1-DNA moiety, eGFP (Enhanced Green Fluorescent Protein) moiety, LysoTracker Green moiety, GFP (S65T) moiety, BODIPY FL, MeOH moiety, Sapphire moiety, BODIPY FL conjugate moiety, MitoTracker Green moiety, MitoTracker Green FM, MeOH moiety, Fluorescein 0.1 M NaOH moiety, Calcein pH 9.0 moiety, Fluorescein pH 9.0 moiety, Calcein moiety, Fura-2, no Ca moiety, Fluo-4 moiety, FDA moiety, DTAF moiety, Fluorescein moiety, CFDA moiety, FITC moiety, Alexa Fluor 488 hydrazide-water moiety, DyLight 488 moiety, 5-FAM pH 9.0 moiety, Alexa 488 moiety, Rhodamine 110 moiety, Rhodamine 110 pH 7.0 moiety, Acridine Orange moiety, BCECF pH 5.5 moiety, PicoGreendsDNA quantitation reagent moiety, SYBR Green I moiety, Rhodaminen Green pH 7.0 moiety, CyQUANT GR-DNA moiety, NeuroTrace 500/525, green fluorescent Nissl stain-RNA moiety, DansylCadaverine moiety, Fluoro-Emerald moiety, Nissl moiety, Fluorescein dextran pH 8.0 moiety, Rhodamine Green moiety, 5-(and -6)-Carboxy-2',7'-dichlorofluorescein pH 9.0 moiety, DansylCadaverine, MeOH moiety, eYFP (Enhanced Yellow Fluorescent Protein) moiety, Oregon Green 488 moiety, Fluo-3 moiety, BCECF pH 9.0 moiety, SBFI-Na+ moiety, Fluo-3 Ca2+ moiety, Rhodamine 123 MeOH moiety, FlAsH moiety, Calcium Green-1 Ca2+ moiety, Magnesium Green moiety, DM-NERF pH 4.0 moiety, Calcium Green moiety, Citrine moiety, LysoSensor Yellow pH 9.0 moiety, TO-PRO-1-DNA moiety, Magnesium Green Mg2+ moiety, Sodium Green Na+ moiety, TOTO-1-DNA moiety, Oregon Green 514 moiety, Oregon Green 514 antibody conjugate pH 8.0 moiety, NBD-X moiety, DM-NERF pH 7.0 moiety, NBD-X, MeOH moiety, CI-NERF pH 6.0 moiety, Alexa 430 moiety, CI-NERF pH 2.5 moiety, Lucifer Yellow, CH moiety, LysoSensor Yellow pH 3.0 moiety, 6-TET, SE pH 9.0 moiety, Eosin antibody conjugate pH 8.0 moiety, Eosin moiety, 6-Carboxyrhodamine 6G pH 7.0 moiety, 6-Carboxyrhodamine 6G, hydrochloride moiety, Bodipy R6G SE moiety, BODIPY R6G MeOH moiety, 6 JOE moiety, Cascade Yellow moiety, mBanana moiety, Alexa 532 moiety, Erythrosin-5-isothiocyanate pH 9.0 moiety, 6-HEX, SE pH 9.0 moiety, mOrange moiety, mHoneydew moiety, Cy 3 moiety, Rhodamine B moiety, DiI moiety, 5-TAMRA-MeOH moiety, Alexa 555 moiety, DyLight 549 moiety, BODIPY TMR-X, SE moiety, BODIPY TMR-X MeOH moiety, PO-PRO-3-DNA moiety, PO-PRO-3 moiety, Rhodamine moiety, POPO-3 moiety, Alexa 546 moiety, Calcium Orange Ca2+ moiety, TRITC moiety, Calcium Orange moiety, Rhodaminephalloidin pH 7.0 moiety, MitoTracker Orange moiety, MitoTracker Orange MeOH moiety, Phycoerythrin moiety, Magnesium Orange moiety, R-Phycoerythrin pH 7.5 moiety, 5-TAMRA pH 7.0 moiety, 5-TAMRA moiety, Rhod-2 moiety, FM 1-43 moiety, Rhod-2 Ca2+ moiety, FM 1-43 lipid moiety, LOLO-1-DNA moiety, dTomato moiety, DsRed moiety, Dapoxyl (2-aminoethyl) sulfonamide moiety, Tetramethylrhodamine dextran pH 7.0 moiety, Fluor-Ruby moiety, Resorufin moiety, Resorufin pH 9.0 moiety, mTangerine moiety, LysoTracker Red moiety, Lissaminerhodamine moiety, Cy 3.5 moiety, Rhodamine Red-X antibody conjugate pH 8.0 moiety, Sulforhodamine 101 EtOH moiety, JC-1 pH 8.2 moiety, JC-1 moiety, mStrawberry moiety, MitoTracker Red moiety, MitoTracker Red, MeOH moiety, X-Rhod-1 Ca2+ moiety, Alexa 568 moiety, 5-ROX pH 7.0 moiety, 5-ROX (5-Carboxy-X-rhodamine, triethylammonium salt) moiety, BO-PRO-3-DNA moiety, BOPRO-3 moiety, BOBO-3-DNA moiety, Ethidium Bromide moiety, ReAsH moiety, Calcium Crimson moiety, Calcium Crimson Ca2+ moiety, mRFP moiety, mCherry moiety, HcRed moiety, DyLight 594 moiety, Ethidium homodimer-1-DNA moiety, Ethidiumhomodimer moiety, Propidium Iodide moiety, SYPRO Ruby moiety, Propidium Iodide-DNA moiety, Alexa 594 moiety, BODIPY TR-X, SE moiety, BODIPY TR-X, MeOH moiety, BODIPY TR-X phallacidin pH 7.0 moiety, Alexa Fluor 610 R-phycoerythrin streptavidin pH 7.2 moiety, YO-PRO-3-DNA moiety, Di-8 ANEPPS moiety, Di-8-ANEPPS-lipid moiety, YOYO-3-DNA moiety, Nile Red-lipid moiety, Nile Red moiety, DyLight 633 moiety, mPlum moiety, TO-PRO-3-DNA moiety, DDAO pH 9.0 moiety, Fura Red high Ca moiety, Allophycocyanin pH 7.5 moiety, APC (allophycocyanin) moiety, Nile Blue, EtOH moiety, TOTO-3-DNA moiety, Cy 5 moiety, BODIPY 650/665-X, MeOH moiety, Alexa Fluor 647 R-phycoerythrin streptavidin pH 7.2 moiety, DyLight 649 moiety, Alexa 647 moiety, Fura Red Ca2+ moiety, Atto 647 moiety, Fura Red, low Ca moiety, Carboxynaphthofluorescein pH 10.0 moiety, Alexa 660 moiety, Cy 5.5 moiety, Alexa 680 moiety, DyLight 680 moiety, Alexa 700 moiety, FM 4-64, 2% CHAPS moiety, or FM 4-64 moiety. In embodiments, the dectable moiety is a moiety of 1,1-Diethyl-4,4-carbocyanine iodide, 1,2-Diphenylacetylene, 1,4-Diphenylbutadiene, 1,4-Diphenylbutadiyne, 1,6-Diphenylhexatriene, 1,6-Diphenyl-hexatriene, 1-anilinonaphthalene-8-sulfonic acid, 2,7-Dichlorofluorescein, 2,5-DIPHENYLOXAZOLE, 2-Di-1-ASP, 2-dodecylresorufin, 2-Methylbenzoxazole, 3,3-Diethylthiadicarbocyanine iodide, 4-Dimethylamino-4-Nitrostilbene, 5(6)-Carboxyfluorescein, 5(6)-Carboxynaphtofluorescein, 5(6)-Carboxytetramethylrhodamine B, 5-(and -6)-carboxy-2',7'-dichlorofluorescein, 5-(and -6)-carboxy-2,7-dichlorofluorescein, 5-(N-hexadecanoyl)aminoeosin, 5-(N-hexadecanoyl)aminoeosin, 5-chloromethylfluorescein, 5-FAM, 5-ROX, 5-TAMRA, 5-TAMRA, 6,8-difluoro-7-hydroxy-4-methylcoumarin, 6,8-difluoro-7-hydroxy-4-methylcoumarin, 6-carboxyrhodamine 6G, 6-HEX, 6-JOE, 6-JOE, 6-TET, 7-aminoactinomycin D, 7-Benzylamino-4-Nitrobenz-2-Oxa-1,3-Diazole, 7-Methoxycoumarin-4-Acetic Acid, 8-Benzyloxy-5,7-diphenylquinoline, 8-Benzyloxy-5,7-diphenylquinoline, 9,10-Bis(Phenylethynyl)Anthracene, 9,10-Diphenylanthracene, 9-METHYLCARBAZOLE, (CS)2Ir(µ-Cl)2Ir(CS)2, AAA, Acridine Orange, Acridine Orange, Acridine Yellow, Acridine Yellow, Adams Apple Red 680, Adirondack Green 520, Alexa Fluor 350, Alexa Fluor 405, Alexa Fluor 430, Alexa Fluor 430, Alexa Fluor 480, Alexa Fluor 488, Alexa Fluor 488, Alexa Fluor 488 hydrazide, Alexa Fluor 500, Alexa Fluor 514, Alexa Fluor 532, Alexa Fluor 546, Alexa Fluor 546, Alexa Fluor 555, Alexa Fluor 555, Alexa Fluor 568, Alexa Fluor 594, Alexa Fluor 594, Alexa Fluor 594, Alexa Fluor 610, Alexa Fluor 610-R-PE, Alexa Fluor 633, Alexa Fluor 635, Alexa Fluor 647, Alexa Fluor 647, Alexa Fluor 647-R-PE, Alexa Fluor 660, Alexa Fluor 680, Alexa Fluor 680-APC, Alexa Fluor 680-R-PE, Alexa Fluor 700, Alexa Fluor 750, Alexa Fluor 790, Allophycocyanin, AmCyanl, Aminomethylcoumarin, Amplex Gold (product), Amplex Red Reagent, Amplex UltraRed, Anthracene, APC, APC-Seta-750, AsRed2, ATTO 390, ATTO 425, ATTO 430LS, ATTO 465, ATTO 488, ATTO 490LS, ATTO 495, ATTO 514, ATTO 520, ATTO 532, ATTO 550, ATTO 565, ATTO 590, ATTO 594, ATTO 610, ATTO 620, ATTO 633, ATTO 635, ATTO 647, ATTO 647N, ATTO 655, ATTO 665, ATTO 680, ATTO 700, ATTO 725, ATTO 740, ATTO Oxa12, ATTO Rho3B, ATTO Rho6G, ATTO Rho11, ATTO Rho12, ATTO Rho13, ATTO Rho14, ATTO Rho101, ATTO Thio12, Auramine O, Azami Green, Azami Green monomeric, B-phycoerythrin, BCECF, BCECF, Bex1, Biphenyl, Birch Yellow 580, Blue-green algae, BO-PRO-1, BO-PRO-3, BOBO-1, BOBO-3, BODIPY 630 650-X, BODIPY 650/665-X, BODIPY FL, BODIPY FL, BODIPY R6G, BODIPY TMR-X, BODIPY TR-X, BODIPY TR-X Ph 7.0, BODIPY TR-X phallacidin, BODIPY-DiMe, BODIPY-Phenyl, BODIPY-TMSCC, C3-Indocyanine, C3-Indocyanine, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, C545T, C-Phycocyanin, Calcein, Calcein red-orange, Calcium Crimson, Calcium Green-1, Calcium Orange, Calcofluor white 2MR, Carboxy SNARF-1 pH 6.0, Carboxy SNARF-1 pH 9.0, Carboxynaphthofluorescein, Cascade Blue, Cascade Yellow, Catskill Green 540, CBQCA, CellMask Orange, CellTrace BODIPY TR methyl ester, CellTrace calcein violet, CellTrace™ Far Red, CellTracker Blue, CellTracker Red CMTPX, CellTracker Violet BMQC, CF405M, CF405S, CF488A, CF543, CF555, CFP, CFSE, CF™ 350, CF™ 485, Chlorophyll A, Chlorophyll B, Chromeo 488, Chromeo 494, Chromeo 505, Chromeo 546, Chromeo 642, Citrine, Citrine, ClOH butoxy aza-BODIPY, ClOH C12 aza-BODIPY, CM-H2DCFDA, Coumarin 1, Coumarin 6, Coumarin 6, Coumarin 30, Coumarin 314, Coumarin 334, Coumarin 343, Coumarine 545T, Cresyl Violet Perchlorate, CryptoLight CF1, CryptoLight CF2, CryptoLight CF3, CryptoLight CF4, CryptoLight CF5, CryptoLight CF6, Crystal Violet, Cumarin153, Cy2, Cy3, Cy3, Cy3.5, Cy3B, Cy3B, Cy3Cy5 ET, Cy5, Cy5, Cy5.5, Cy7, Cyanine3 NHS ester, Cyanine5 carboxylic acid, Cyanine5 NHS ester, Cyclotella meneghiniana Ktitzing, CypHer5, CypHer5 pH 9.15, CyQUANT GR, CyTrak Orange, Dabcyl SE, DAF-FM, DAMC (Weiss), dansyl cadaverine, Dansyl Glycine (Dioxane), DAPI, DAPI, DAPI, DAPI, DAPI (DMSO), DAPI (H2O), Dapoxyl (2-aminoethyl)sulfonamide, DCI, DCM, DCM, DCM (acetonitrile), DCM (MeOH), DDAO, Deep Purple, di-8-ANEPPS, DiA, Dichlorotris(1,10-phenanthroline) ruthenium(II), DiClOH C12 aza-BODIPY, DiClOHbutoxy aza-BODIPY, DiD, DiI, DiIC18(3), DiO, DiR, Diversa Cyan-FP, Diversa Green-FP, DM-NERF pH 4.0, DOCI, Doxorubicin, DPP pH-Probe 590-7.5, DPP pH-Probe 590-9.0, DPP pH-Probe 590-11.0, DPP pH-Probe 590-11.0, Dragon Green, DRAQ5, DsRed, DsRed, DsRed, DsRed-Express, DsRed-Express2, DsRed-Express T1, dTomato, DY-350XL, DY-480, DY-480XL MegaStokes, DY-485, DY-485XL MegaStokes, DY-490, DY-490XL MegaStokes, DY-500, DY-500XL MegaStokes, DY-520, DY-520XL MegaStokes, DY-547, DY-549P1, DY-549P1, DY-554, DY-555, DY-557, DY-557, DY-590, DY-590, DY-615, DY-630, DY-631, DY-633, DY-635, DY-636, DY-647, DY-649P1, DY-649P1, DY-650, DY-651, DY-656, DY-673, DY-675, DY-676, DY-680, DY-681, DY-700, DY-701, DY-730, DY-731, DY-750, DY-751, DY-776, DY-782, Dye-28, Dye-33, Dye-45, Dye-304, Dye-1041, DyLight 488, DyLight 549, DyLight 594, DyLight 633, DyLight 649, DyLight 680, E2-Crimson, E2-Orange, E2-Red/Green, EBFP, ECF, ECFP, ECL Plus, eGFP, ELF 97, Emerald, Envy Green, Eosin, Eosin Y, epicocconone, EqFP611, Erythrosin-5-isothiocyanate, Ethidium bromide, ethidium homodimer-1, Ethyl Eosin, Ethyl Eosin, Ethyl Nile Blue A, Ethyl-p-Dimethylaminobenzoate, Ethyl-p-Dimethylaminobenzoate, Eu2O3 nanoparticles, Eu (Soini), Eu(tta) 3DEADIT, EvaGreen, EVOblue-30, EYFP, FAD, FITC, FITC, FlAsH (Adams), Flash Red EX, F1AsH-CCPGCC, F1AsH-CCXXCC, Fluo-3, Fluo-4, Fluo-5F, Fluorescein, Fluorescein 0.1 NaOH, Fluorescein-Dibase, fluoro-emerald, Fluorol 5G, FluoSpheres blue, FluoSpheres crimson, FluoSpheres dark red, FluoSpheres orange, FluoSpheres red, FluoSpheres yellow-green, FM4-64 in CTC, FM4-64 in SDS, FM 1-43, FM 4-64, Fort Orange 600, Fura Red, Fura Red Ca free, fura-2, Fura-2 Ca free, Gadodiamide, Gd-Dtpa-Bma, Gadodiamide, Gd-Dtpa-Bma, GelGreen™, GelRed™, H9-40, HcRedl, Hemo Red 720, HiLyte Fluor 488, HiLyte Fluor 555, HiLyte Fluor 647, HiLyte Fluor 680, HiLyte Fluor 750, HiLyte Plus 555, HiLyte Plus 647, HiLyte Plus 750, HmGFP, Hoechst 33258, Hoechst 33342, Hoechst-33258, Hoechst-33258, Hops Yellow 560, HPTS, HPTS, HPTS, HPTS, HPTS, indo-1, Indo-1 Ca free, Ir(Cn)2(acac), Ir(Cs)2(acac), IR-775 chloride, IR-806, Ir-OEP-CO-C1, IRDye® 650 Alkyne, IRDye® 650 Azide, IRDye® 650 Carboxylate, IRDye® 650 DBCO, IRDye® 650 Maleimide, IRDye® 650 NHS Ester, IRDye® 680LT Carboxylate, IRDye® 680LT Maleimide, IRDye® 680LT NHS Ester, IRDye® 680RD Alkyne, IRDye® 680RD Azide, IRDye® 680RD Carboxylate, IRDye® 680RD DBCO, IRDye® 680RD Maleimide, IRDye® 680RD NHS Ester, IRDye®

700 phosphoramidite, IRDye® 700DX, IRDye® 700DX, IRDye® 700DX Carboxylate, IRDye® 700DX NHS Ester, IRDye® 750 Carboxylate, IRDye® 750 Maleimide, IRDye® 750 NHS Ester, IRDye® 800 phosphoramidite, IRDye® 800CW, IRDye® 800CW Alkyne, IRDye® 800CW Azide, IRDye® 800CW Carboxylate, IRDye® 800CW DBCO, IRDye® 800CW Maleimide, IRDye® 800CW NHS Ester, IRDye® 800RS, IRDye® 800RS Carboxylate, IRDye® 800RS NHS Ester, IRDye® QC-1 Carboxylate, IRDye® QC-1 NHS Ester, *Isochrysis galbana*—Parke, JC-1, JC-1, JOJO-1, Jonamac Red Evitag T2, Kaede Green, Kaede Red, kusabira orange, Lake Placid 490, LDS 751, Lissamine Rhodamine (Weiss), LOLO-1, lucifer yellow CH, Lucifer Yellow CH, lucifer yellow CH, Lucifer Yellow CH Dilitium salt, Lumio Green, Lumio Red, Lumogen F Orange, Lumogen Red F300, Lumogen Red F300, LysoSensor Blue DND-192, LysoSensor Green DND-153, LysoSensor Green DND-153, LysoSensor Yellow/Blue DND-160 pH 3, LysoSensor YellowBlue DND-160, LysoTracker Blue DND-22, LysoTracker Blue DND-22, LysoTracker Green DND-26, LysoTracker Red DND-99, LysoTracker Yellow HCK-123, Macoun Red Evitag T2, Macrolex Fluorescence Red G, Macrolex Fluorescence Yellow 10GN, Macrolex Fluorescence Yellow 10GN, Magnesium Green, Magnesium Octaethylporphyrin, Magnesium Orange, Magnesium Phthalocyanine, Magnesium Phthalocyanine, Magnesium Tetramesitylporphyrin, Magnesium Tetraphenylporphyrin, malachite green isothiocyanate, Maple Red-Orange 620, Marina Blue, mBanana, mBBr, mCherry, Merocyanine 540, Methyl green, Methyl green, Methyl green, Methylene Blue, Methylene Blue, mHoneyDew, MitoTracker Deep Red 633, MitoTracker Green FM, MitoTracker Orange CMTMRos, MitoTracker Red CMXRos, monobromobimane, Monochlorobimane, Monoraphidium, mOrange, mOrange2, mPlum, mRaspberry, mRFP, mRFP1, mRFP1.2 (Wang), mStrawberry (Shaner), mTangerine (Shaner), N,N-Bis(2,4,6-trimethylphenyl)-3,4:9,10-perylenebis(dicarboximide), NADH, Naphthalene, Naphthalene, Naphthofluorescein, Naphthofluorescein, NBD-X, NeuroTrace 500525, Nilblau perchlorate, nile blue, Nile Blue, Nile Blue (EtOH), nile red, Nile Red, Nile Red, Nile red, Nileblue A, NIR1, NIR2, NIR3, NIR4, NIR820, Octaethylporphyrin, OH butoxy aza-BODIPY, OHC12 aza-BODIPY, Orange Fluorescent Protein, Oregon Green 488, Oregon Green 488 DHPE, Oregon Green 514, Oxazin1, Oxazin 750, Oxazine 1, Oxazine 170, P4-3, P-Quaterphenyl, P-Terphenyl, PA-GFP (post-activation), PA-GFP (pre-activation), Pacific Orange, Palladium (II) meso-tetraphenyl-tetrabenzoporphyrin, PdOEPK, PdTFPP, PerCP-Cy5.5, Perylene, Perylene, Perylene bisimide pH-Probe 550-5.0, Perylene bisimide pH-Probe 550-5.5, Perylene bisimide pH-Probe 550-6.5, Perylene Green pH-Probe 720-5.5, Perylene Green Tag pH-Probe 720-6.0, Perylene Orange pH-Probe 550-2.0, Perylene Orange Tag 550, Perylene Red pH-Probe 600-5.5, Perylenediimid, Perylne Green pH-Probe 740-5.5, Phenol, Phenylalanine, pHrodo, succinimidyl ester, Phthalocyanine, PicoGreen dsDNA quantitation reagent, Pinacyanol-lodide, Piroxicam, Platinum(II) tetraphenyltetrabenzoporphyrin, Plum Purple, PO-PRO-1, PO-PRO-3, POPO-1, POPO-3, POPOP, Porphin, PPO, Proflavin, PromoFluor-350, PromoFluor-405, PromoFluor-415, PromoFluor-488, PromoFluor-488 Premium, PromoFluor-488LSS, PromoFluor-500LSS, PromoFluor-505, PromoFluor-510LSS, PromoFluor-514LSS, PromoFluor-520LSS, PromoFluor-532, PromoFluor-546, PromoFluor-555, PromoFluor-590, PromoFluor-610, PromoFluor-633, PromoFluor-647, PromoFluor-670, PromoFluor-680, PromoFluor-700, PromoFluor-750, PromoFluor-770, PromoFluor-780, PromoFluor-840, propidium iodide, Protoporphyrin IX, PTIR475/UF, PTIR545/UF, PtOEP, PtOEPK, PtTFPP, Pyrene, QD525, QD565, QD585, QD605, QD655, QD705, QD800, QD903, QD PbS 950, QDot 525, QDot 545, QDot 565, Qdot 585, Qdot 605, Qdot 625, Qdot 655, Qdot 705, Qdot 800, QpyMe2, QSY 7, QSY 7, QSY 9, QSY 21, QSY 35, quinine, Quinine Sulfate, Quinine sulfate, R-phycoerythrin, R-phycoerythrin, ReAsH-CCPGCC, ReAsH-CCXXCC, Red Beads (Weiss), Redmond Red, Resorufin, resorufin, rhod-2, Rhodamin 700 perchlorate, rhodamine, Rhodamine 6G, Rhodamine 6G, Rhodamine 101, rhodamine 110, Rhodamine 123, rhodamine 123, Rhodamine B, Rhodamine B, Rhodamine Green, Rhodamine pH-Probe 585-7.0, Rhodamine pH-Probe 585-7.5, Rhodamine phalloidin, Rhodamine Red-X, Rhodamine Red-X, Rhodamine Tag pH-Probe 585-7.0, Rhodol Green, Riboflavin, Rose Bengal, Sapphire, SBFI, SBFI Zero Na, *Scenedesmus* sp., SensiLight PBXL-1, SensiLight PBXL-3, Seta 633-NHS, Seta-633-NHS, SeTau-380-NHS, SeTau-647-NHS, Snake-Eye Red 900, SNIR1, SNIR2, SNIR3, SNIR4, Sodium Green, Solophenyl flavine 7GFE 500, Spectrum Aqua, Spectrum Blue, Spectrum FRed, Spectrum Gold, Spectrum Green, Spectrum Orange, Spectrum Red, Squarylium dye III, Stains All, Stilben derivate, Stilbene, Styryl8 perchlorate, Sulfo-Cyanine3 carboxylic acid, Sulfo-Cyanine3 carboxylic acid, Sulfo-Cyanine3 NHS ester, Sulfo-Cyanine5 carboxylic acid, Sulforhodamine 101, sulforhodamine 101, Sulforhodamine B, Sulforhodamine G, Suncoast Yellow, SuperGlo BFP, SuperGlo GFP, Surf Green EX, SYBR Gold nucleic acid gel stain, SYBR Green I, SYPRO Ruby, SYTO 9, SYTO 11, SYTO 13, SYTO 16, SYTO 17, SYTO 45, SYTO 59, SYTO 60, SYTO 61, SYTO 62, SYTO 82, SYTO RNASelect, SYTO RNASelect, SYTOX Blue, SYTOX Green, SYTOX Orange, SYTOX Red, T-Sapphire, Tb (Soini), tCO, tdTomato, Terrylen, Terrylendiimid, testdye, Tetra-t-Butylazaporphine, Tetra-t-Butylnaphthalocyanine, Tetracen, Tetrakis(o-Aminophenyl)Porphyrin, Tetramesitylporphyrin, Tetramethylrhodamine, tetramethylrhodamine, Tetraphenylporphyrin, Tetraphenylporphyrin, Texas Red, Texas Red DHPE, Texas Red-X, ThiolTracker Violet, Thionin acetate, TMRE, TO-PRO-1, TO-PRO-3, Toluene, Topaz (Tsien1998), TOTO-1, TOTO-3, Tris(2,2-Bipyridyl)Ruthenium(II) chloride, Tris(4,4-diphenyl-2,2-bipyridine) ruthenium(II) chloride, Tris(4,7-diphenyl-1,10-phenanthroline) ruthenium(II) TMS, TRITC (Weiss), TRITC Dextran (Weiss), Tryptophan, Tyrosine, Vex 1, Vybrant DyeCycle Green stain, Vybrant DyeCycle Orange stain, Vybrant DyeCycle Violet stain, WEGFP (post-activation), WellRED D2, WellRED D3, WellRED D4, WtGFP, WtGFP (Tsien1998), X-rhod-1, Yakima Yellow, YFP, YO-PRO-1, YO-PRO-3, YOYO-1, YoYo-1, YoYo-1 dsDNA, YoYo-1 ssDNA, YOYO-3, Zinc Octaethylporphyrin, Zinc Phthalocyanine, Zinc Tetramesitylporphyrin, Zinc Tetraphenylporphyrin, ZsGreen1, or ZsYellow1.

In embodiments, the detectable label is a fluorescent dye. In embodiments, the detectable label is a fluorescent dye capable of exchanging energy with another fluorescent dye (e.g., fluorescence resonance energy transfer (FRET) chromophores).

In embodiments, the detectable moiety is a moiety of a derivative of one of the detectable moieties described immediately above, wherein the derivative differs from one of the detectable moieties immediately above by a modification resulting from the conjugation of the detectable moiety to a compound described herein.

The term "mass label" means a molecular entity of a known or predetermined mass that is capable of being covalently attached, preferably via by a cleavable bond, to another chemical compound, e.g., a protein, nucleotide, etc.

The term "nucleotide" is defined herein to include both nucleotides and nucleosides, including deoxynucleotides, ribonucleotides, and analogues thereof. Nucleosides, as for nucleotides, comprise a purine or pyrimidine base linked glycosidically to ribose or deoxyribose, but they lack the phosphate residues that would make them a nucleotide. Synthetic and naturally occurring nucleotides are included within the definition, as are those that are labeled and/or blocked. The term "nucleoside" includes natural nucleosides, including 2'-deoxy and 2'-hydroxyl forms, e.g. as described in Kornberg and Baker, DNA Replication, 2nd Ed. (Freeman, San Francisco, 1992), as well as non-naturally occurring forms, for example, a 7-deazapurine base, a pyrazole[3,4-d]pyrimidine base, a propynyl-dN base, or other analogues or derivatives known in the art. "Analogues" in reference to nucleosides include synthetic nucleosides having modified base moieties and/or modified sugar moieties, see, e.g., Scheit, Nucleotide Analogues (John Wiley, New York, 1980); Uhlman and Peyman, Chemical Reviews, 90:543-584 (1990), or the like, with the only proviso that they are capable of specific hybridization to a complementary base in another DNA molecule. Such analogues include synthetic nucleosides designed to enhance binding properties, reduce complexity, increase specificity, and the like.

The term "oligonucleotide" includes linear oligomers of natural or non-natural nucleotide monomers or linkages, including deoxyribonucleosides, ribonucleosides, anomeric forms thereof, peptide nucleic acids (PNAs), and the like, capable of specifically binding to a target polynucleotide by way of a regular pattern of monomer-to-monomer interactions, such as Watson-Crick type of base pairing and the like. Usually monomers are linked by phosphodiester bonds or analogues thereof to form oligonucleotides ranging in size from a few monomeric units, e.g., 3-10, to several tens of monomeric units, e.g., 20-100. Whenever an oligonucleotide (or other nucleic acid) is represented by a sequence of letters, such as "ATGCCTG", it will be understood that the nucleotides are in 5'-3' orientation from left to right and that "A" denotes adenine or an analogue thereof, "C" denotes cytosine or an analogue thereof, "G" denotes guanine or an analogue thereof, and "T" denotes thymine or an analogue thereof, unless otherwise noted. Usually oligonucleotides of the present disclosure comprise the four (or five) natural nucleotides; however, they may also comprise non-natural nucleotide analogues.

The term "population" refers to a collection of one or more entities, e.g., DNA molecules.

"Perfectly matched" in reference to a nucleic acid duplex means that the poly- or oligonucleotide strands making up the duplex form a double-stranded structure, or region of double-stranded structure, with one another such that every nucleotide (or nucleotide analogue) in each strand undergoes Watson-Crick base-pairing with a nucleotide in the other strand in the duplexed (i.e., hybridized) region. The term also encompasses the pairing of nucleoside analogues, such as deoxyinosine, nucleosides with 2-aminopurine bases, and the like. Conversely, a "mismatch" in a nucleic acid duplex means that one or more pairs of nucleotides in the duplex fail to undergo Watson-Crick base-pairing.

The term "radiolabel" refers to an isotopic label such as a naturally non-abundant radioactive or heavy isotope, including but not limited to $^{14}C$, $^{123}I$, $^{124}I$, $^{125}I$, $^{131}I$, $^{32}P$, $^{35}S$, and $^{3}H$.

A "removable" group, e.g., a label or a blocking group, refers to a chemical group that can be removed from a dNTP analogue or extension product such that a DNA polymerase can extend the nucleic acid (e.g., a primer or extension product) by the incorporation of at least one additional nucleotide. Removal may be by any suitable method, including enzymatic, chemical, or photolytic cleavage. Removal of a removable group, e.g., a blocking group, does not require that all of the removable group be removed, only that a sufficient portion of it be removed such that a DNA polymerase can extend a nucleic acid by incorporation of at least one additional nucleotide or dNTP analogue.

The terms "sequencing", "sequence determination", "determining a nucleotide sequence", and the like include determination of partial as well as full sequence information of the polynucleotide being sequenced. That is, the term includes sequence comparisons, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide.

The term "sequencing reaction mixture" refers to an aqueous mixture that contains the reagents necessary to allow a dNTP or dNTP analogue to be incorporated into a DNA strand by a DNA polymerase.

The term "solid substrate" means any suitable medium present in the solid phase to which an antibody or an agent can be covalently or non-covalently affixed or immobilized.

The term "species", when used in the context of describing a particular compound or molecule species, refers to a population of chemically indistinct molecules.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the present disclosure. The upper and lower limits of any such smaller range (within a more broadly recited range) may independently be included in the smaller ranges, or as particular values themselves, and are also encompassed within the present disclosure, subject to any specifically excluded limit in the stated range. Where the stated range includes one or both of the limits, ranges excluding either or both of those included limits are also included in the present disclosure.

As used herein, the singular forms "a", "an", and "the" include plural references unless the context clearly dictates otherwise.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

As used herein, the term "distinguishable" (e.g., in reference to dNTP analogues and/or extension products) refers to a molecule which can be differentiated from other similar molecules. That is, the molecule is distinctive and discernable from the other similar molecules. With respect to dNTP analogues, for example, dATP analogues, dGTP analogues, dCTP analogues, dTTP analogues and/or dUTP analogues, the identity of each dNTP analogue may be distinguishable from each other dNTP analogue based on (for example and without limitation) the type and/or intensity of a label associated with each dNTP analogue.

As used herein, the term "primed template DNA molecule" refers to a template DNA molecule which is associated with a primer (a short polynucleotide) that can serve as a starting point for DNA synthesis.

As used herein, the term "incorporable" when used to describe a nucleotide or analogue refers to a nucleotide or analogue which can be used to extend a primer or an extension product.

The terms "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite (Na2S2O4), hydrazine (N2H4)). A chemically cleavable linker is non-enzymatically cleavable. In embodiments, the cleavable linker is cleaved by contacting the cleavable linker with a cleaving agent. In embodiments, the cleaving agent is sodium dithionite (Na2S2O4), weak acid, hydrazine (N2H4), Pd(0), or light-irradiation (e.g., ultraviolet radiation). In embodiments, the cleavable moiety is a polymerase-compatible cleavable moiety.

A photocleavable linker (e.g., including or consisting of a o-nitrobenzyl group) refers to a linker which is capable of being split in response to photo-irradiation (e.g., ultraviolet radiation). An acid-cleavable linker refers to a linker which is capable of being split in response to a change in the pH (e.g., increased acidity). A base-cleavable linker refers to a linker which is capable of being split in response to a change in the pH (e.g., decreased acidity). An oxidant-cleavable linker refers to a linker which is capable of being split in response to the presence of an oxidizing agent. A reductant-cleavable linker refers to a linker which is capable of being split in response to the presence of a reducing agent (e.g., Tris(3-hydroxypropyl)phosphine). In embodiments, the cleavable linker is a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

The term "polymerase-compatible cleavable moiety" as used herein refers a cleavable moiety which does not interfere with the function of a polymerase (e.g., DNA polymerase, modified DNA polymerase). Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible cleavable moiety does not decrease the function of a polymerase relative to the absence of the polymerase-compatible cleavable moiety. In embodiments, the polymerase-compatible cleavable moiety does not negatively affect DNA polymerase recognition. In embodiments, the polymerase-compatible cleavable moiety does not negatively affect (e.g., limit) the read length of the DNA polymerase. Additional examples of a polymerase-compatible cleavable moiety may be found in U.S. Pat. No. 6,664,079, Ju J. et al. (2006) *Proc Natl Acad Sci USA* 103(52): 19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218): 53-59; or Hutter D. et al. (2010) *Nucleosides Nucleotides & Nucleic Acids* 29:879-895, which are incorporated herein by reference in their entirety for all purposes. In embodiments, a polymerase-compatible cleavable moiety includes an azido moiety or a dithiol linking moiety. In embodiments, the polymerase-compatible cleavable moiety is $-NH_2$, $-CN$, $-CH_3$, $C_2$-$C_6$ allyl (e.g., $-CH_2-CH=CH_2$), methoxyalkyl (e.g., $-CH_2-O-CH_3$), or $-CH_2N_3$. In embodiments, the polymerase-compatible cleavable moiety comprises a disulfide moiety.

The term "DNA polymerase" and "nucleic acid polymerase" are used in accordance with their plain ordinary meaning and refer to enzymes capable of synthesizing nucleic acid molecules from nucelotides (e.g., deoxyribonucleotides). Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g., Taq polymerase, Terminator γ, 9° N polymerase (exo-), Therminator II, Therminator III, or Therminator IX).

The term "thermophilic nucleic acid polymerase" as used herein refers to a family of DNA polymerases (e.g., 9°N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M W, et al. *PNAS*. 1996; 93(11):5281-5285). A thermophilic nucleic acid polymerase is a member of the family B DNA polymerases. Site-directed mutagenesis of the 3'-5' exo motif I (Asp-Ile-Glu) to Asp-Ile-Asp resulted in reduction of 3'-5' exonuclease activity to <1% of wild-type, while maintaining other properties of the polymerase including its high strand displacement activity. Subsequent mutagenesis of key amino acids results in an increased ability of the enzyme to incorporate dideoxynucleotides, ribonucleotides and acyclonucleotides (e.g., Therminator II enzyme from New England Biolabs with D141A/E143A/Y409V/A485L mutations); 3'-amino-dNTPs, 3'-azido-dNTPs and other 3'-modified nucleotides (e.g., NEB Therminator III DNA Polymerase with D141A/E143A/L408S/Y409A/P410V mutations, NEB Therminator IX DNA polymerase), or γ-phosphate labeled nucleotides (e.g., Therminator γ: D141A/E143A/W355A/L408W/R460A/Q461S/K464E/D480V/R484W/A485L).

Typically these enzymes do not have 5'-3' exonuclease activity. Additional information about thermophilic nucleic acid polymerases may be found in (Southworth M W, et al. *PNAS*. 1996; 93(11):5281-5285; Bergen K, et al. *ChemBioChem*. 2013; 14(9):1058-1062; Kumar S, et al. *Scientific Reports*. 2012; 2:684; Fuller C W, et al. 2016; 113(19):5233-5238; Guo J, et al. *Proceedings of the National Academy of Sciences of the United States of America*. 2008; 105(27): 9145-9150), which are incorporated herein in their entirety for all purposes.

II. Sequence-by-Synthesis Methods

The present disclosure provides methods for determining the identity of one or more nucleotide residues in an extension product. Such methods can be used, for example, to determine the sequence of target DNA, including partial and whole genomes, exomes, transcriptomes, and the like. Such methods comprise combining in a sequencing reaction mixture a plurality of identical primed template DNA molecules, a DNA polymerase, at least 4 distinguishable, blocked deoxyribonucleotide triphosphate (dNTP) analogue species, at least 3 of which are labeled such that various distinguishable, blocked dNTP analogue species can be distinguished from the other such species, under conditions to allow incorporation of one of the distinguishable, blocked dNTP analogue species into at least some of the plurality of identical primed template DNA molecules to form a (or a population of) distinguishable, blocked extension product(s). In embodiments, a distinguishable, blocked dNTP analogue species is incorporated into less than about 95%, 90%, 85%, 80%, 75%, 70%, 65%, 60%, 55%, 50%, 45%, 40%, 35%, 30%, 25%, or 20% of the plurality of identical primed template DNA molecules.

In embodiments, the template DNA molecules are either in solution or immobilized on a solid substrate, wherein the solid substrate optionally is gold, quartz, silica, plastic (e.g., polypropylene), glass, diamond, silver, or metal and optionally is configured as a bead, chip, well, wafer, filter, or slide. When the solid substrate is glass, template DNA molecule immobilization methods include the use of hydrogels or direct covalent linkage, for example, using silanes, e.g., amino-silanes, epoxy-silanes, and aldehyde-silanes. Additionally, when the DNA template molecules optionally are attached/bound to the solid substrate by covalent site-specific coupling chemistry compatible with DNA, other suitable chemistries include (i) alkyne-labeled, (ii) bound to the solid substrate via polyethylene glycol (PEG) molecules and the solid substrate is azide-functionalized, or (iii) immobilized on the solid substrate via an azido linkage, or an alkynyl linkage. Other representative embodiments of non-covalent attachment include those based on biotin-streptavidin interactions. In embodiments, solid substrate is a porous medium.

In embodiments of the methods of the present disclosure, the DNA polymerase is a 9° N polymerase or variant thereof. In other embodiments, DNA polymerases that can be used in the instant disclosure include, for example *E. coli* DNA polymerase I, bacteriophage T4 DNA polymerase, SEQUENASE™ (genetically engineered T7 DNA polymerase having little to no 3' to 5' exonuclease activity; ThermoFisher Scientific), and Taq DNA polymerase, or a variant of each thereof.

In embodiments, the distinguishable, blocked dNTP analogue species in the reaction mixture include four (or five) species of labeled, blocked dNTP analogues, such as a labeled, blocked dGTP analogue, a labeled, blocked dATP analogue, a labeled, blocked dCTP analogue, and a labeled, blocked dTTP analogue and/or a labeled, blocked dUTP analogue. In embodiments, the labeled, blocked dNTP analogues are 3'-blocked dNTP analogues, although 2'- and/or 4'-blocked dNTP analogues can also be used, alone, together, or in combination with 3'-blocked dNTP analogues, although in such embodiments the reversible chemistry used for blocking moieties is the same in order to facilitate unblocking of the dNTP analogue for extension in a subsequent SBS cycle.

In embodiments, the label moiety(ies) of each such dNTP analogue species is(are) unique so as to allow that dNTP analogue species to be distinguished from the other dNTP analogue species present in the sequencing reaction mixture, although in embodiments two of the dNTP analogue species, e.g., dTTP and dUTP, are present and include the same label species. In other embodiments, such as those wherein fewer than 4 channels are used in for detection, fewer than 4 different label species can be used. For example, in some 2-channel SBS methods that employ 4 distinguishable, blocked dNTP analogue species, the first dNTP analogue species is unlabeled, the second dNTP analogue species includes a first label moiety, the third dNTP analogue species includes a second label moiety that is different and distinguishable from the first label moiety, and the fourth distinguishable, blocked dNTP analogue species includes the first and second label moieties, allowing it to be distinguished from the second and third dNTP analogue species. In this way, all 4 of these dNTP species can be distinguished from each other. Regarding the distinguishable, blocked dNTP analogue species that is unlabeled in such embodiments, its identity for cycles in which no detection was observed can be inferred if in a subsequent SBS cycle a base containing one or two label moieties is detected. In other 2 channel SBS methods, different ratios of two fluorescent dyes may be used to distinguish the four bases. For example, one dNTP species could be labeled only with label A, a second dNTP species could be labeled only with label B, and the third and fourth dNTP species could be labeled with different ratios of labels A and B. For example, the third dNTP species could be labeled with a mixture of 70% label A and 30% label B, and the fourth dNTP species could be labeled with a mixture of 70% label B and 30% label A. In still other embodiments, different ratios of a single label (or different ratios of a single label and no label) could be used so as to allow 1-channel detection to be used. For example, one dNTP species could be labeled with a dye (e.g., using 4 of the same dye molecules) to yield 100% signal intensity, a second dNTP species could be labeled with the dye (e.g., using 3 of the same dye molecules) to yield 75% signal intensity, a third dNTP species could be labeled with the dye (e.g., using 2 of the same dye molecules) to yield 50% signal intensity, and the fourth dNTP species could be labeled with the dye (e.g., using 1 of the same dye molecules) to yield 25% signal intensity.

In embodiments, the labeled, 3'-blocked dNTP analogues are a labeled, 3'-blocked dGTP analogue, a labeled, 3'-blocked dCTP analogue, a labeled, 3'-blocked dATP analogue, and a labeled, 3'-blocked dTTP analogue and/or a labeled, 3'-blocked dUTP analogue. In embodiments, the labeled, 3'-blocked dGTP, dCTP, dATP, dTTP, and/or dUTP analogue(s) comprise an incorporable nucleoside or incorporable analogue thereof. In embodiments, such incorporable nucleoside or incorporable analogue thereof comprises a base selected from the group consisting of guanine (in the case of a labeled, 3'-blocked dGTP analogue), cytosine (in the case of a labeled, 3'-blocked dCTP analogue), adenine (in the case of a labeled, 3'-blocked dATP analogue), thymine (in the case of a labeled, 3'-blocked dTTP analogue), or uracil (in the case of a labeled, 3'-blocked dUTP analogue). In embodiments, the labeled, 3'-blocked dGTP, dCTP, dATP, dTTP, and/or dUTP analogue(s) comprise a sugar moiety that is deoxyribose or a deoxyribose analogue. In embodiments, the labeled, 3'-blocked dGTP, dCTP, dATP, dTTP, and/or dUTP analogue(s) comprise a cleavable blocking moiety, wherein the cleavable blocking moiety optionally is linked to the 3'-position of the sugar moiety. In embodiments, the sugar moiety is deoxyribose or a deoxyribose analogue.

In embodiments, each of the labeled, 3'-blocked dNTP analogue species is distinguishable from the other labeled, 3'-blocked dNTP analogue species by inclusion of a unique label molecule that differs from the unique label molecules of the other labeled, 3'-blocked dNTP analogue species. In embodiments, the label molecules are selected from the group consisting of a dye, a chromophore, a combinatorial fluorescence energy transfer label, an electrophore, a fluorophore, a mass label, and a radiolabel. In embodiments, the cleavable blocking moiety is chemically cleavable or is a photocleavable linker. In embodiments, the cleavable blocking moiety is linked to the 3'-position of the sugar moiety (optionally a deoxyribose or a deoxyribose analogue) and comprises the unique label molecule. Methods for production of cleavably blocked and/or cleavably linked nucleotide analogues are described in, for example, U.S. Pat. No. 6,664,079, which is incorporated herein by reference in its entirety.

Labeled, 3'-blocked dNTP analogues that may be used in the methods described herein include, without limitation, 3'-O-allyl-dGTP-allyl-Cy5, 3'-O-allyl-dCTP-allyl-Bodipy-FL-510, 3'-O-allyl-dATP-allyl-ROX, and 3'-O-allyl-dUTP-allyl-R6G; 3'-O-allyl-dGTP-allyl-Bodipy-FL-510, 3'-O-allyl-dCTP-allyl-Bodipy-650, 3'-O-allyl-dATP-allyl-ROX, and 3'-O-allyl-dUTP-allyl-R6G; and 3'-O-allyl-dGTP-allyl-Bodipy-650, 3'-O-allyl-dCTP-allyl-Bodipy-FL-510, 3'-O-allyl-dATP-allyl-ROX, and 3'-O-allyl-dUTP-allyl-R6G. See, e.g., U.S. Pat. Nos. 7,883,869, 8,298,792, and 9,528,151, each of which is incorporated herein by reference in its entirety.

Although generally described herein using a cleavable linker, it is understood that a cleavable linker is not required so long as a signal from the label attached to nucleic acid molecule can be reduced. For example, the signal from a dye can be reduced by chemical quenching, thermal quenching, photobleaching, and the like. A label can also be removed or modified by cleaving the label while leaving the linker intact, so long as the detectable signal from the label (e.g., a dye) is reduced sufficiently to allow identification of a subsequently added label molecule on an extended nucleic acid chain. For example, a protease-cleavable peptide linkage can be used. At each polymerase extension cycle, only one nucleotide will be incorporated. In embodiments using fluorescent labels, a fluorescent image is taken to determine which base has been incorporated based on the color codes. In embodiments, the label molecules can be cleaved by a protease link to the distinguishable, blocked dNTP analogue via a peptide bond, and the blocking group can be subsequently or simultaneously removed (as can occur if both cleavage reactions are enzymatic reactions and can be carried out in the same buffer). Once the label and blocking groups are removed, the next SBS cycle can be initiated.

In embodiments of the methods of the present disclosure, the cleavable blocking moiety of the distinguishable, blocked dNTP analogues is linked to the 3'-oxygen of a deoxyribose via an allyl moiety or a 2-nitrobenzyl moiety, for example, 3'-O-2-nitrobenzyl-dGTP-allyl-Bodipy-650, 3'-O-2-nitrobenzyl-dGTP-2-nitrobenzyl-Bodipy-650, and 3'-O-allyl-dGTP-2-nitrobenzyl-Bodipy-650. The cleavable linkage can be chemically cleavable or photocleavable.

Additional blocked nucleoside and nucleotide molecules for use in the methods described herein can be found, for example, in U.S. Pat. Nos. 9,593,373 and 8,399,188; and PCT Patent Pub. Nos. WO 2017/058953 and WO 2017/205336; each of which is incorporated herein by reference in its entirety.

After forming the distinguishable, blocked extension product(s), the methods of the present disclosure include either removing the initial sequencing reaction mixture and replacing it with a chasing reaction mixture or adding to the sequencing reaction mixture at least 4 unlabeled, blocked dNTP analogue species under chasing conditions (i.e., conditions under which an unlabeled, blocked dNTP analogue species can be incorporated into a primed template DNA molecule that was not extended to include a distinguishable, blocked dNTP analogue species), thereby forming the unlabeled, blocked extension product(s). In the event a chasing reaction mixture is used after removing the initial sequencing reaction mixture, the chasing reaction mixture will be understood to include all the reagents necessary, including a DNA polymerase (or other catalyst that promotes the addition of the appropriate dNTP to the 3'-OH of a primer or extension product associated with a template DNA molecule), to allow incorporation of an unlabeled, blocked dNTP analogue species into a growing DNA strand that is complementary to the template DNA molecule, as chasing is designed to ensure the efficient production of extension products in a given SBS cycle so that they may be unblocked and used to perform a subsequent SBS cycle and so on, up through the number of cycles to be run. As will be appreciated, extension of all primed DNA template molecules, and their extension products, is critical to ensure accurate DNA sequencing.

In embodiments of the present disclosure, the at least 4 unlabeled, blocked dNTP analogue species are added to the sequencing reaction mixture to allow chasing before the sequencing reaction (i.e., the reaction in which a distinguishable, blocked dNTP is incorporated) runs to completion or the sequencing reaction is otherwise terminated, for example, by washing and/or removal and replacement of the sequencing reaction mixture with a chasing reaction mixture prior to its completion. In those embodiments where the sequencing reaction is terminated prior to running to completion, a chasing reaction mixture is added (or otherwise created). In embodiments, the chasing reaction is initiated before the sequencing reaction is complete (i.e., 95%-100% of the primed template DNA molecules have incorporated a distinguishable, blocked dNTP) but after a sufficient percentage of the primed template DNA molecules have been extended by incorporating distinguishable, blocked dNTPs so that the identity of the added dNTP can be determined. In embodiments, the chasing reaction is initiated after the sequencing reaction is about 25% to less than 95% complete, about 40% to about 80% complete, about 45% to about 75% complete, or about 50% to about 70% complete. In embodiments, the chasing reaction is initiated after the sequencing reaction is about 50% complete. Completion of the sequencing reaction may include any value or subrange within the recited ranges, including endpoints.

In embodiments, the methods described herein result in a sequencing cycle (e.g., cycle including extension, chase, image, cleave, and/or wash/fluid movement steps) between about 1 minute and about 40 minutes long. In embodiments, the sequencing cycle is between about 1 minute and about 30 minutes long. In embodiments, the sequencing cycle is between about 1 minute and about 20 minutes long. In embodiments, the sequencing cycle is between about 1 minute and about 15 minutes long. In embodiments, the sequencing cycle is between about 1 minute and about 10 minutes long. In embodiments, the sequencing cycle is between about 1 minute and about 5 minutes long. The length of the sequencing cycle may include any value or subrange within the recited ranges, including endpoints.

In embodiments, the methods described herein result in combined extension, chase, and image steps within a cycle of between about 1 minute and about 20 minutes long. In embodiments, the combined extension, chase, and image steps within a cycle is between about 1 minute and about 15 minutes long. In embodiments, the combined extension, chase, and image steps within a cycle is between about 1 minute and about 10 minutes long. In embodiments, the combined extension, chase, and image steps within a cycle is between about 1 minute and about 5 minutes long. The length of the combined extension, chase, and image steps within a cycle may include any value or subrange within the recited ranges, including endpoints.

In embodiments, the methods described herein result in a sequencing cycle that is at least about 10%, at least about 20%, at least about 30%, at least about 40%, at least about 50%, or at least about 60% faster than a conventional SBS sequencing cycle (e.g., a sequencing cycle that does not include simultaneous imaging during step (a) or step (b)). In embodiments, the methods described herein result in a combined extension, chase, and image steps within a cycle that is at least about 10%, at least about 20%, at least about 30%, at least about 40%, at least about 50%, or at least about 60% faster than a conventional SBS sequencing cycle. In embodiments, the methods described herein result in a total sequencing reaction (i.e., having "n" iterations) that is at least about 10%, at least about 20%, at least about 30%, at least about 40%, at least about 50%, or at least about 60% faster than a conventional SBS sequencing cycle (having "n" iterations).

In embodiments, the unlabeled, blocked dNTP analogue species are 3'-OH blocked. In other embodiments, the blocking moiety may be attached at the 2'- or 4'-position of the sugar moiety. 3'-blocked dNTP analogue species that may be used in the methods described herein include, without limitation, an unlabeled, 3'-blocked dGTP, an unlabeled, 3'-blocked dCTP, an unlabeled, 3'-blocked dATP, and an unlabeled, 3'-blocked dTTP or an unlabeled, 3'-blocked dUTP, wherein optionally the unlabeled, 3'-blocked dNTPs comprise an incorporable nucleoside or incorporable analogue thereof. In embodiments, such incorporable nucleoside or incorporable analogue thereof comprises guanine (in the case of an unlabeled, 3'-blocked dGTP), cytosine (in the case of an unlabeled, 3'-blocked dCTP), adenine (in the case of an unlabeled, 3'-blocked dATP), thymine (in the case of an unlabeled, 3'-blocked dTTP), or uracil (in the case of an unlabeled, 3'-blocked dUTP), the unlabeled, 3'-blocked dNTP analogues comprise a sugar moiety that is deoxyribose or a deoxyribose analogue. In embodiments, the unlabeled, 3'-blocked dNTP analogues comprise a cleavable blocking moiety, wherein the cleavable blocking moiety optionally is linked to the 3'-position of the sugar moiety. In embodiments, the sugar moiety is deoxyribose or a deoxyribose analogue. In embodiments, the cleavable blocking moiety of the unlabeled, 3'-blocked dNTP analogues is linked to the 3'-oxygen of a deoxyribose via an allyl moiety or a 2-nitrobenzyl moiety.

Unlabeled, 3'-blocked dNTP analogues that may be used in the methods described herein include, without limitation, 3'-O-allyl-dGTP, 3'-O-allyl-dCTP, 3'-O-allyl-dATP, and 3'-O-allyl-dUTP; and 3'-O-2-nitrobenzyl-dGTP, 3'-O-2-nitrobenzyl-dCTP, 3'-O-2-nitrobenzyl-dATP, and 3'-O-2-nitrobenzyl-dUTP.

In order to decrease SBS cycle times, in embodiments of the present disclosure the identity of distinguishable, blocked dNTP analogue incorporated into the labeled, blocked extension product(s) generated in the sequencing reaction of such cycle is assessed while the sequencing reaction is running, i.e., before the chasing reaction is initiated. In other embodiments, such assessment is conducted during the chasing reaction. In embodiments, such assessment is conducted about less than 60 seconds before termination of the sequencing reaction, about less than 60 seconds before initiation of the chasing reaction, about less than 300 seconds after initiation of the chasing reaction, or about less than 60 to about less than 10 seconds before termination of the chasing reaction. In embodiments, such assessment is conducted substantially simultaneously with initiation of the chasing reaction. In embodiments, such assessment is conducted at the conclusion of or after the chasing reaction.

In an embodiment, the method further comprises assigning the complement of the labeled, 3'-blocked dNTP analogue incorporated in the distinguishable, blocked extension product as the identity of the nucleotide residue in the template DNA molecule. In other embodiments, the identity of the distinguishable, blocked (e.g., labeled, 3'-blocked) dNTP analogue is assigned as the identity of the nucleotide residue. This process may be iterated one or more times.

In embodiments, the methods of the present disclosure further comprise treating the distinguishable (e.g., labeled) and unlabeled, blocked extension products to generate extendible, unlabeled extension products. Representative examples of such treatment include cleavage, optionally chemical, enzymatic, or photoactivated cleavage, of a blocking moiety linked, for example, to a 3'-oxygen atom of a terminal deoxyribose of the distinguishable, blocked extension products and unlabeled, blocked extension products (if any) and of the label molecules of the distinguishable, blocked extension products. In embodiments, the system is engineered such that the same cleavage treatment can be used to remove the blocking moiety and the label moiety.

In embodiments, the methods further comprise removing unbound distinguishable, blocked dNTP analogues before initiating the chasing reaction.

Embodiments of this aspect involve iterating the foregoing steps (sequencing reaction, chasing reaction, base identification, etc.) one or more times, wherein after nucleotide identification of each iteration, the distinguishable, blocked extension products and unlabeled, blocked extension products are treated to generate extendible extension products and to remove label moieties, with the proviso that after the last iteration, treatment of the labeled and unlabeled, blocked extension products can be omitted.

The present disclosure also provides nucleic acid sequencing-by-synthesis methods for a DNA template molecule, comprising iterating the sequencing, chasing, and base identification steps, above, two or more times; after each iteration, treating the distinguishable, blocked extension products and unlabeled, blocked extension products to generate extendible extension products, with the proviso that after the last iteration, treatment of the extension products can be omitted; for each iteration, assigning the complement of the distinguishable, blocked dNTP analogue determined in the identification step as the identity of the nucleotide residue in the template DNA molecule for that iteration; and assembling in order (optionally 5' to 3') the identities of the nucleotide residues of the template DNA molecule, thereby determining by synthesis the nucleotide sequence of the template DNA molecule.

In embodiments where the sequence of a nucleic acid molecule is to be determined, SBS cycles can be repeated or iterated. Each SBS cycle can include any number of steps for determining the identity of a nucleotide at a particular sequence location. For example, in embodiments utilizing dNTP analogues having a blocking group and an enzymatically cleavable label, each cycle can include the steps of adding such a nucleotide to a primer or extension product using a sequencing reaction and a chasing reaction (which can be included as part of the sequencing reaction, but after the sequencing reaction has been initiated and allowed to run for some time but not to completion), detecting the label on the primer, and then removing the label and blocking groups either in the same or separate reactions. Cycles can be repeated to determine a sequence present in a template to which a primer is hybridized. The number of cycles performed in a sequencing method can be at least 10, 25, 50, 75, 100, 150, 200, 250, or more. Cycles can be repeated until a predetermined length of sequence has been determined including, for example, until a desired sequence length, for example, 25, 50, 75, 100, 150, 200, 250, 500, or 1,000 nucleotides, has been determined. The above-described ranges are merely exemplary and are not intended to limit the use of the methods. It will be understood that any number of cycles can be performed as desired, for example, within a perceived or accepted limit of detection for the embodiment employed.

In another aspect, the present disclosure provides kits for performing a method according to the present disclosure. In general, such kits will include, optionally in separate containers or compartments, (a) distinguishable, blocked dNTP analogues, for example, labeled, 3'-blocked dNTP analogues such labeled, 3'-blocked dGTP, dATP, dCTP, and dTTP and/or dUTP analogues, (b) unlabeled, blocked dNTP analogues, for example, unlabeled, 3'-blocked dGTP, dATP, dCTP, and dTTP and/or dUTP analogues, (c) reagents suitable for use in DNA synthesis, and (d) instructions (or a link other reference to a website providing such instructions) for using such dNTP analogues and reagents to perform a method of the present disclosure.

One consideration in SBS sequencing approaches is the set of modified nucleotides (e.g., dATP, dGTP, dTTP (and/or dUTP), dCTP analogues) selected for use, as these distinguishable, blocked dNTP analogues must be capable of being efficiently incorporated into DNA strands by a DNA polymerase and also be capable of having the blocking group and, optionally, the label, removed readily after incorporation. In embodiments, the blocking moiety and label are attached to the nucleotide at the same location, while in other embodiments, they are attached at different locations, optionally via the same type of linking group so that each of the blocking and label moieties can be removed by the same process, although in embodiments, different cleavable linking chemistries can be employed for the blocking and label moieties of a given distinguishable, blocked dNTP analogue. In addition, because the present disclosure also employs unlabeled, blocked dNTP analogues as "chasing" reagents (i.e., reagents used to drive an incomplete reaction to completion), selection of the set of unlabeled, blocked dNTP analogues is a consideration. In embodiments, the unlabeled, blocked dNTP analogues used to chase a sequencing reaction to completion in an SBS cycle will be unlabeled analogues of the distinguishable, blocked dNTP analogues used in the sequencing reaction portion of the particular SBS cycle.

Many of the distinguishable, blocked dNTP analogues for SBS are modified at the 3'-OH position of 2'-deoxynucleoside triphosphates, although such 3' modifications are known to inhibit the activity of many DNA polymerases, although a number of modified DNA polymerases have been developed to overcome, at least to some degree, such inhibition. Indeed, some 3' modified nucleotide analogues with small modifiers, such as an allyl group, are efficiently accepted by DNA polymerases engineered to include mutations in their nucleotide binding sites.

As an alternative to 3'-OH modifications of the sugar ring of a dNTP, a blocking group (or a blocking group and a label, or a label that also serves as a blocking group) can be placed at an alternate position of a nucleotide, such as 2' or 4', such that the nucleotide can be efficiently incorporated but also effectively block incorporation of the next nucleotide. These blocking groups (which may also be labels, i.e., a "blocking label" group or moiety) can have properties, for example, charge, hydrophobicity, hydrophilicity, or size, that effectively terminates the polymerase elongation or extension reaction but allows sufficient recognition and efficient polymerase-mediated incorporation of the dNTP analogue into an extension product. The blocking group can subsequently be cleaved or otherwise removed. Such modified nucleotides are referred to herein as a 2'- or 4'-blocked (and/or labeled or distinguishable) dNTP analogues. Exemplary 2'- and 4'-blocked distinguishable dNTP analogues are described in published U.S. patent application publication no. 2017/0029883, which is incorporated herein by reference in its entirety. Unlabeled analogues of such distinguishable 2'- and 4'-blocked dNTP analogues can also be prepared for use as chasing reagents. Such distinguishable and unlabeled dNTP analogues include allyl, acetal, aminal, sulfate, phosphate, and thial groups as blocking moieties.

Following incorporation of such dNTP analogues by a DNA polymerase in an SBS cycle, the blocking group can be removed, for example, photolytically, chemically, or enzymatically. It should be noted that the atom attached to the C2' or C4' carbon atom does not have to be oxygen since the only requirement is that the change induced during the deblocking step should transform the incorporated dNTP analogue nucleotide into a nucleotide that can be further extended in an subsequent SBS cycle. It is understood that the blocking groups used as 2' blocking groups can also be used as 4' blocking groups. Particularly useful conditions for removing the terminator moiety include those that preserve hybridization of the primer or extension product to the template DNA, although other methods that require a hairpin (e.g., via a palindromic sequence) to link the primer covalently to the template DNA can also be used.

Example 1

DNA Sequencing with Simultaneous Imaging and Chase Steps

Figure 1:
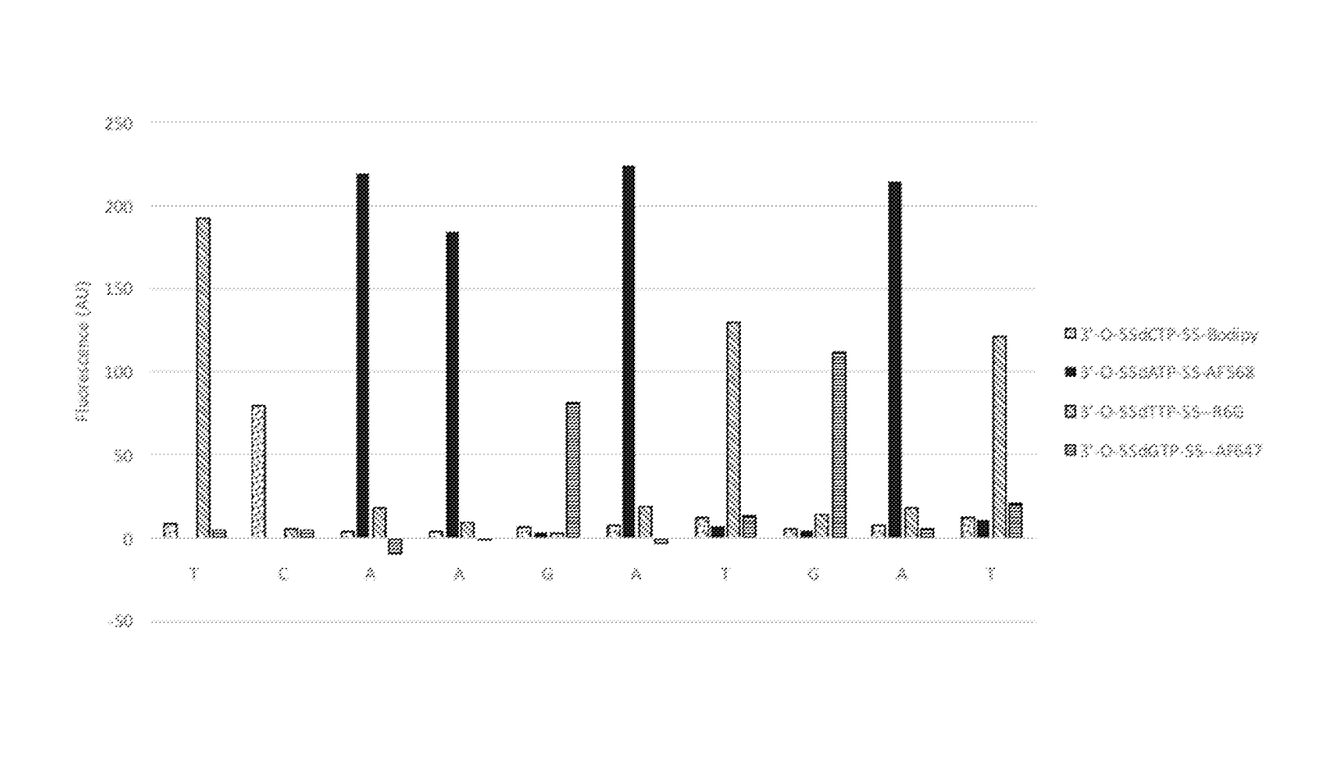

Provided here is an example of the embodiment of a sequencing-by-synthesis method where the DNA bases were identified during the chase step. In this example, identical DNA fragments derived from the PhiX 174 genome were immobilized on 1 micron beads. The beads were tethered to a glass coverslip which was part of a flow cell. All necessary reagents for SBS were sequentially delivered into the flow cell. At first, four distinguishable, blocked dNTP analogues were presented into the flow cell. Each dNTP was labeled with a different fluorophore as follows: dCTP-Bodipy, dTTP-R6G, dATP-AF568, dGTP-AF647. A sequencing polymerase was used to incorporate these dNTPs into the complementary strand. A small volume of buffer was then used to remove any excess dye-labeled, blocked dNTPs. As a second step, dark, blocked dNTPs were introduced into the flow cell. During this second step, a set of four images was taken, one for each of the colors corresponding to each dye-labeled dNTP, while the dark dNTPs continued to be incorporated into any unextended DNA templates on the bead. The images were obtained using a Nikon microscope, with a 20×0.75 NA objective, and standard filter sets corresponding to each of the dyes. Note that the images were taken simultaneously with the chasing step, at a temperature of 60° C., demonstrating the compatibility of the two processes in terms of reaction conditions. The excess dark, blocked dNTPs were then washed out and a deprotection reagent was brought in. This reagent cleaved the blocking group and the dye from the incorporated dNTPs. The cycle was then repeated as many times as desirable. The results from the first 10 cycles obtained using this method are shown in FIG. 1. Each bar represents the fluorescent signal from the corresponding base. Spectral cross-talk correction, which compensates for the spectral bleed through from one emission channel into another, was applied to these data. No additional corrections have been applied. We have shown sequencing read lengths of >75 bases in this manner.

All of the articles, devices, systems, and methods disclosed and claimed herein can be made and executed without undue experimentation in light of the present disclosure. While the devices, systems, and methods of the present disclosure have been described in terms of various embodiments, it will be apparent to those of skill in the art that variations may be applied to the articles and methods without departing from the spirit and scope of the present disclosure. All such variations and equivalents apparent to those skilled in the art, whether now existing or later developed, are deemed to be within the spirit and scope of the present disclosure as defined by the appended claims. It will also be appreciated that computer-based embodiments of the instant disclosure can be implemented using any suitable hardware and software.

All patents, patent applications, and publications mentioned in the specification are indicative of the levels of those of ordinary skill in the art to which the present disclosure pertains. All patents, patent applications, and publications are herein incorporated by reference in their entirety for all purposes and to the same extent as if each individual publication was specifically and individually indicated to be incorporated by reference in its entirety for any and all purposes.

The present disclosure illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by various embodiments and optional features, modification and variation of the concepts herein disclosed may be resorted to by those skilled in the art, and that such modifications and variations are considered to be within the scope of the present disclosure as defined by the appended claims.

What is claimed is:

1. A method to determine the identity of a nucleotide residue in an extension product, comprising:
   (a) combining in a sequencing reaction mixture a plurality of identical primed template DNA molecules, a DNA polymerase, at least 4 distinguishable, blocked deoxyribonucleotide triphosphate (dNTP) analogue species, at least 3 of which distinguishable, blocked dNTP analogue species are labeled such that each distinguishable, blocked dNTP analogue species in the sequencing reaction mixture can be distinguished from the other distinguishable, blocked dNTP analogue species, thereby incorporating a distinguishable, blocked dNTP analogue species into at least one of said plurality of identical primed template DNA molecules and forming a distinguishable, blocked extension product; and
   (b) after step (a), removing unincorporated distinguishable, blocked dNTP analogues followed by adding to the sequencing reaction mixture at least 4 unlabeled, blocked dNTP analogue species, incorporating an unlabeled, blocked dNTP analogue species into at least one of said plurality of identical primed template DNA molecules thereby forming an unlabeled, blocked extension product; and
   (c) upon addition of the at least 4 unlabeled, blocked dNTP analogue species during step (b), determining the identity of the distinguishable, blocked dNTP analogue incorporated into the distinguishable, blocked extension product in step (a), wherein the combined steps (a)-(c) occurs for about 1 minute to about 10 minutes.

2. The method according to claim 1 further comprising assigning the complement of the distinguishable, blocked dNTP analogue determined in step (c) as the identity of the nucleotide residue in the template DNA molecule.

3. The method according to claim 2 comprising iterating steps (a)-(c) one or more times, thereby determining a nucleotide sequence of at least a portion of the template DNA molecule.

4. The method according to claim 1 that, after step (c), further comprises (d) chemical, enzymatic, or photoactivated cleavage, of a blocking moiety linked to a 3'-oxygen atom of a terminal deoxyribose of the distinguishable, blocked extension products and/or unlabeled, blocked extension products to generate extensible extension products.

5. The method according to claim 1 that comprises iterating steps (a)-(c) one or more times, wherein after step (c) of each iteration, the distinguishable, blocked extension products and unlabeled, blocked extension products are treated to generate extendible extension products, with the proviso that after the last iteration, treatment of distinguishable, blocked extension products and unlabeled, blocked extension products can be omitted.

6. The method according to claim 1 wherein the labeled, 3'-blocked dNTP analogues are:
   (i) a labeled, 3'-blocked dGTP analogue;
   (ii) a labeled, 3'-blocked dCTP analogue;
   (iii) a labeled, 3'-blocked dATP analogue; and
   (iv) a labeled, 3'-blocked dTTP analogue or a labeled, 3'-blocked dUTP analogue;
   wherein the labeled, 3'-blocked dGTP, dCTP, dATP, dTTP, and/or dUTP analogue(s) comprise:
      an incorporable nucleoside or incorporable analogue thereof; the labeled, 3'-blocked dGTP, dCTP, dATP, dTTP, and/or dUTP analogue(s) comprise a sugar moiety that is deoxyribose or a deoxyribose analogue;
      a cleavable blocking moiety, wherein the cleavable blocking moiety optionally is linked to the 3'-position of the sugar moiety, wherein the sugar moiety optionally is deoxyribose or a deoxyribose analogue; and a unique label molecule that differs from the unique label molecules of each of the other labeled, 3'-blocked dNTP analogue species such that each of the labeled, 3'-blocked dNTP analogue species is distinguishable from the other labeled, 3'-blocked dNTP analogue species.

7. The method of claim 6, wherein the label molecules are selected from the group consisting of a dye, a chromophore, a combinatorial fluorescence energy transfer label, an electrophore, a fluorophore, a mass label, and a radiolabel.

8. The method according to claim 6 wherein the cleavable blocking moiety of the labeled, 3'-blocked dNTP analogues is linked to the 3'-oxygen of a deoxyribose via an allyl moiety, a 2-nitrobenzyl moiety, an azido moiety, or a disulfide moiety.

9. The method according to claim 1 wherein the unlabeled, 3'-blocked dNTP analogue species are:
   (i) an unlabeled, 3'-blocked dGTP;
   (ii) an unlabeled, 3'-blocked dCTP;
   (iii) an unlabeled, 3'-blocked dATP; and
   (iv) an unlabeled, 3'-blocked dTTP or an unlabeled, 3'-blocked dUTP;
   wherein the unlabeled, 3'-blocked dNTPs comprise:
      an incorporable nucleoside or incorporable analogue thereof,
      a sugar moiety that is deoxyribose or a deoxyribose analogue; and
      a cleavable blocking moiety, wherein the cleavable blocking moiety is linked to the 3'-position of the sugar moiety.

10. The method according to claim 9 wherein the unlabeled, 3'-blocked dNTP analogues are selected from the group consisting of:
   (i) 3'-O-allyl-dGTP, 3'-O-allyl-dCTP, 3'-O-allyl-dATP, and 3'-O-allyl-dUTP; and
   (ii) 3'-O-2-nitrobenzyl-dGTP, 3'-O-2-nitrobenzyl-dCTP, 3'-O-2-nitrobenzyl-dATP, and 3'-O-2-nitrobenzyl-dUTP.

11. The method according to claim 1, wherein the template DNA molecules are in solution.

12. The method according to claim 1, wherein the template DNA molecules are immobilized on a solid substrate, wherein the DNA template molecules are
   bound to the solid substrate via polyethylene glycol (PEG) molecules and the solid substrate is azide-functionalized; or
   immobilized on the solid substrate via an azido linkage, an alkynyl linkage, or a biotin-streptavidin interaction.

13. The method according to claim 1 configured to use 4-channel detection, 2 channel detection, or 1 channel detection.

14. A method to determine the identity of a nucleotide residue in an extension product, comprising:
   (a) combining in a sequencing reaction mixture a plurality of identical primed template DNA molecules, a DNA polymerase, and labeled, 3'-blocked dNTP analogues consisting of:
      (i) a labeled, 3'-blocked dGTP analogue; and
      (ii) a labeled, 3'-blocked dATP analogue; and
      (iii) a labeled, 3'-blocked dCTP analogue; and
      (iv) a labeled, 3'-blocked dTTP analogue and/or a labeled, 3'-blocked dUTP analogue, thereby incorporating a labeled, 3'-blocked deoxyribonucleotide triphosphate (dNTP) analogue species into at least one of said plurality of identical primed template DNA molecules and forming a labeled, blocked extension product;
   (b) after step (a), removing unincorporated labeled, 3'-blocked dNTP analogues followed by adding to said sequencing reaction mixture unlabeled, 3'-blocked dNTP analogues consisting of:
      (i) an unlabeled, 3'-blocked dGTP analogue; and
      (ii) an unlabeled, 3'-blocked dATP analogue; and
      (iii) an unlabeled, 3'-blocked dCTP analogue; and
      (iv) an unlabeled, 3'-blocked dTTP analogue and/or an unlabeled, 3'-blocked dUTP analogue, incorporating an unlabeled, 3'-blocked dNTP analogue into at least one of said plurality of identical primed template DNA molecules thereby forming an unlabeled, blocked extension product; and
   (c) upon addition of the unlabeled, 3'-blocked dNTP analogues during step (b), determining the identity of the labeled, 3'-blocked dNTP analogue incorporated into the labeled, blocked extension product in step (a), wherein the combined steps (a)-(c) are about 1 minute to about 10 minutes long.

15. A nucleic acid sequencing-by-synthesis method for a DNA template molecule, comprising:
   (i) iterating steps (a)-(c) of claim 1 two or more times;
   (ii) after each iteration, treating the distinguishable, blocked extension products and unlabeled, blocked extension products to generate extendible extension products, with the proviso that after the last iteration, treatment of the distinguishable, blocked extension products and unlabeled, blocked extension products can be omitted;
   (iii) for each iteration, assigning the complement of the distinguishable, blocked dNTP analogue determined in step (c) as the identity of the nucleotide residue in the template DNA molecule for that iteration; and
   (iv) assembling in order the identities of the nucleotide residues of the template DNA molecule, thereby determining by synthesis the nucleotide sequence of the template DNA molecule.

* * * * *